(12) United States Patent
Poeze et al.

(10) Patent No.: US 11,114,188 B2
(45) Date of Patent: Sep. 7, 2021

(54) SYSTEM FOR MONITORING A PHYSIOLOGICAL PARAMETER OF A USER

(71) Applicant: Cercacor Laboratories, Inc., Irvine, CA (US)

(72) Inventors: Jeroen Poeze, Mission Viejo, CA (US); Gregory A. Olsen, Trabuco Canyon, CA (US); Marcelo Lamego, Coto de Caza, CA (US); Massi Joe E. Kiani, Laguna Niguel, CA (US)

(73) Assignee: Cercacor Laboratories, Inc., Irvine, CA (US)

( * ) Notice: Subject to any disclaimer, the term of this patent is extended or adjusted under 35 U.S.C. 154(b) by 0 days.

(21) Appl. No.: 16/219,827

(22) Filed: Dec. 13, 2018

(65) Prior Publication Data

US 2019/0216319 A1 Jul. 18, 2019

Related U.S. Application Data

(63) Continuation of application No. 12/898,663, filed on Oct. 5, 2010, now abandoned.
(Continued)

(51) Int. Cl.
*A61B 5/00* (2006.01)
*G16H 10/60* (2018.01)
(Continued)

(52) U.S. Cl.
CPC ........... *G16H 10/60* (2018.01); *A61B 5/0022* (2013.01); *A61B 5/02241* (2013.01);
(Continued)

(58) Field of Classification Search
USPC .................................................. 600/300–301
See application file for complete search history.

(56) References Cited

U.S. PATENT DOCUMENTS 4,901,728 A 2/1990 Hutchison
4,960,128 A 10/1990 Gordon et al.
(Continued)

OTHER PUBLICATIONS

US 8,845,543 B2, 09/2014, Diab et al. (withdrawn)
(Continued)

*Primary Examiner* — Shirley X Jian
(74) *Attorney, Agent, or Firm* — Knobbe, Martens, Olson & Bear, LLP

(57) ABSTRACT

The present disclosure provides an electronic device that includes at least one sensor indicative of a physiological condition of a user, the at least one sensor worn by a patient. The electronic device can further include a location determination module configured to determine a location of a patient. The electronic device can receive a measured information from the sensor and determine if the physiological condition of the user indicates an urgent medical need. When the physiological condition of the user indicates an urgent medical need, the electronic device can contact emergency services and access and contact one or more of a contact in an electronic address book associated with the processing system. The electronic device can provide a location of the user based on information determined by the location determination module.

6 Claims, 9 Drawing Sheets

Related U.S. Application Data

(60) Provisional application No. 61/249,221, filed on Oct. 6, 2009.

(51) Int. Cl.

| | | |
|---|---|---|
| *A61B 5/145* | (2006.01) | |
| *A61B 5/1455* | (2006.01) | |
| *G16H 50/20* | (2018.01) | |
| *G06Q 10/10* | (2012.01) | |
| *G16H 40/63* | (2018.01) | |
| *A61B 5/022* | (2006.01) | |
| *G16H 10/65* | (2018.01) | |
| *G16H 40/67* | (2018.01) | |

(52) U.S. Cl.
CPC ........ *A61B 5/1455* (2013.01); *A61B 5/14532* (2013.01); *A61B 5/14546* (2013.01); *A61B 5/6825* (2013.01); *A61B 5/7285* (2013.01); *A61B 5/746* (2013.01); *A61B 5/7435* (2013.01); *G06Q 10/10* (2013.01); *G06Q 10/109* (2013.01); *G16H 40/63* (2018.01); *G16H 50/20* (2018.01); *A61B 5/14535* (2013.01); *A61B 5/14552* (2013.01); *A61B 5/6824* (2013.01); *A61B 5/7275* (2013.01); *A61B 5/742* (2013.01); *A61B 5/7475* (2013.01); *A61B 2562/0233* (2013.01); *G16H 10/65* (2018.01); *G16H 40/67* (2018.01)

(56) References Cited

U.S. PATENT DOCUMENTS

| | | | |
|---|---|---|---|
| 4,964,408 A | 10/1990 | Hink et al. | |
| 5,009,230 A | 4/1991 | Hutchinson | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,370,114 A | 12/1994 | Wong et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,509 A | 7/1996 | Koashi et al. | |
| 5,533,511 A | 7/1996 | Kaspari et al. | |
| 5,534,851 A | 7/1996 | Russek | |
| 5,553,616 A | 9/1996 | Ham et al. | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,664,109 A | 9/1997 | Johnson et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,820,622 A | 10/1998 | Gross et al. | |
| 5,823,950 A | 10/1998 | Diab et al. | |
| 5,823,966 A | 10/1998 | Buchert | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,885,211 A | 3/1999 | Eppstein et al. | |
| 5,890,929 A | 4/1999 | Mills et al. | |
| 5,899,855 A | 5/1999 | Brown | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,961,451 A | 10/1999 | Reber et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,061,582 A | 5/2000 | Small et al. | |
| 6,064,896 A | 5/2000 | Rosenthal | |
| 6,066,204 A | 5/2000 | Haven | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,115,673 A | 9/2000 | Malin et al. | |
| 6,124,597 A | 9/2000 | Shehada | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,168,563 B1 | 1/2001 | Brown | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,280,381 B1 | 8/2001 | Malin et al. | |
| 6,285,896 B1 | 9/2001 | Tobler et al. | |
| 6,295,506 B1 | 9/2001 | Heinonen et al. | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |

(56) References Cited

U.S. PATENT DOCUMENTS

| | | |
|---|---|---|
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,477,393 B1 | 11/2002 | Chou |
| 6,487,429 B2 | 11/2002 | Hockersmith et al. |
| 6,494,830 B1 | 12/2002 | Wessel |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,561,978 B1 | 5/2003 | Conn et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,641,533 B2 | 11/2003 | Causey, III et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,656,114 B1 | 12/2003 | Pulsen et al. |
| 6,658,276 B2 | 12/2003 | Kianl et al. |
| 6,661,161 B1 | 12/2003 | Lanzo et al. |
| 6,662,030 B2 | 12/2003 | Khalil et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,691,043 B2 | 2/2004 | Ribeiro, Jr. |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,188 B2 | 3/2004 | Wessel |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,748,250 B1 | 6/2004 | Berman et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,809,653 B1 | 10/2004 | Mann et al. |
| 6,813,511 B2 | 11/2004 | Diab et al. |
| 6,816,241 B2 | 11/2004 | Grubisic |
| 6,816,741 B2 | 11/2004 | Diab |
| 6,819,950 B2 | 11/2004 | Mills |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,451 B2 | 5/2005 | Wuori |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,949,070 B2 | 9/2005 | Ishler |
| 6,950,687 B2 | 9/2005 | Al-Ali |
| 6,954,662 B2 | 10/2005 | Freger et al. |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,163,511 B2 | 1/2007 | Conn et al. |
| 7,179,226 B2 | 2/2007 | Crothall et al. |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,231,263 B2 | 6/2007 | Choi |
| 7,239,905 B2 | 7/2007 | Kiani-Azarbayjany et al. |
| 7,241,265 B2 | 7/2007 | Cummings et al. |
| 7,245,953 B1 | 7/2007 | Parker |
| 7,248,907 B2 | 7/2007 | Hogan |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| 7,344,500 B2 | 3/2008 | Talbot et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |

(56) References Cited

U.S. PATENT DOCUMENTS

| | | | |
|---|---|---|---|
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,400,257 B2 | 7/2008 | Rivas |
| 7,403,805 B2 | 7/2008 | Abreu |
| 7,415,297 B2 | 8/2008 | Al-Ali et al. |
| 7,428,432 B2 | 9/2008 | Ali et al. |
| 7,430,445 B2 | 9/2008 | Esenaliev et al. |
| 7,438,683 B2 | 10/2008 | Al-Ali et al. |
| 7,440,786 B2 | 10/2008 | Hockersmith et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,327 B2 | 4/2009 | White |
| 7,519,406 B2 | 4/2009 | Blank et al. |
| 7,526,328 B2 | 4/2009 | Diab et al. |
| D592,507 S | 5/2009 | Wachman et al. |
| 7,529,537 B2 * | 5/2009 | Ford ............... H04W 4/90 |
| | | 455/404.1 |
| 7,530,942 B1 | 5/2009 | Diab |
| 7,530,949 B2 | 5/2009 | Al Ali et al. |
| 7,530,955 B2 | 5/2009 | Diab et al. |
| 7,539,532 B2 * | 5/2009 | Tran ............... A61B 5/021 |
| | | 600/509 |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,601,123 B2 | 10/2009 | Tweed et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| 7,689,202 B2 * | 3/2010 | Ford ............... H04W 4/90 |
| | | 455/404.1 |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,726,209 B2 | 6/2010 | Ruotoistenmäki |
| 7,729,733 B2 | 6/2010 | Al-Ali et al. |
| 7,734,320 B2 | 6/2010 | Al-Ali |
| 7,739,130 B2 | 6/2010 | Surwit et al. |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,862,523 B2 | 1/2011 | Ruotoistenmaki |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,289,130 B2 | 10/2012 | Nakajima et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,323,189 B2 * | 12/2012 | Tran ............... A61B 5/0024 |
| | | 600/300 |

(56) References Cited

U.S. PATENT DOCUMENTS

| | | |
|---|---|---|
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,364,389 B2 | 1/2013 | Dorogusker et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,615,290 B2 | 12/2013 | Lin et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,655,004 B2 | 2/2014 | Prest et al. |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,760,517 B2 | 6/2014 | Sarwar et al. |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtzuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,437 B2 | 7/2015 | Paalasmaa |
| 9,072,474 B2 | 7/2015 | Al-Ali et al. |
| 9,078,560 B2 | 7/2015 | Schurman et al. |
| 9,081,889 B2 | 7/2015 | Ingrassia, Jr. et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |

(56) References Cited

U.S. PATENT DOCUMENTS

| | | |
|---|---|---|
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,210,566 B2 | 12/2015 | Ziemianska et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,311,382 B2 | 4/2016 | Varoglu et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,357,665 B2 | 5/2016 | Myers et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,489,081 B2 | 11/2016 | Anzures et al. |
| 9,492,110 B2 | 11/2016 | Al-Ali et al. |
| 9,497,534 B2 | 11/2016 | Prest et al. |
| 9,510,779 B2 | 12/2016 | Poeze et al. |
| 9,517,024 B2 | 12/2016 | Kiani et al. |
| 9,526,430 B2 | 12/2016 | Srinivas et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,553,625 B2 | 1/2017 | Hatanaka et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,593,969 B2 | 3/2017 | King |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,651,405 B1 | 5/2017 | Gowreesunker et al. |
| 9,662,052 B2 | 5/2017 | Al-Ali et al. |
| 9,668,676 B2 | 6/2017 | Culbert |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,699,546 B2 | 7/2017 | Qian et al. |
| 9,716,937 B2 | 7/2017 | Qian et al. |
| 9,717,425 B2 | 8/2017 | Kiani et al. |
| 9,717,458 B2 | 8/2017 | Lamego et al. |
| 9,723,997 B1 | 8/2017 | Lamego |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,781,984 B2 | 10/2017 | Baranski et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,658 B2 * | 11/2017 | Tran .................. A61B 5/0006 |
| 9,820,691 B2 | 11/2017 | Kiani |
| 9,833,152 B2 | 12/2017 | Kiani et al. |
| 9,833,180 B2 | 12/2017 | Shakespeare et al. |
| 9,838,775 B2 | 12/2017 | Qian et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,848,823 B2 | 12/2017 | Raghuram et al. |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,866,671 B1 | 1/2018 | Thompson et al. |
| 9,867,575 B2 | 1/2018 | Maani et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,898,049 B2 | 2/2018 | Myers et al. |
| 9,913,617 B2 | 3/2018 | Al-Ali et al. |
| 9,918,646 B2 | 3/2018 | Singh Alvarado et al. |
| 9,924,893 B2 | 3/2018 | Schurman et al. |
| 9,924,897 B1 | 3/2018 | Abdul-Hafiz |

(56) References Cited

U.S. PATENT DOCUMENTS

| | | |
|---|---|---|
| 9,936,917 B2 | 4/2018 | Poeze et al. |
| 9,943,269 B2 | 4/2018 | Muhsin et al. |
| 9,949,676 B2 | 4/2018 | Al-Ali |
| 9,952,095 B1 | 4/2018 | Hotelling et al. |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,080 B2 | 7/2018 | Miller et al. |
| 10,039,482 B2 | 8/2018 | Al-Ali et al. |
| 10,052,037 B2 | 8/2018 | Kinast et al. |
| 10,055,121 B2 | 8/2018 | Chaudhri et al. |
| 10,058,275 B2 | 8/2018 | Al-Ali et al. |
| 10,064,562 B2 | 9/2018 | Al-Ali |
| 10,066,970 B2 | 9/2018 | Gowreesunker et al. |
| 10,076,257 B2 | 9/2018 | Lin et al. |
| 10,078,052 B2 | 9/2018 | Ness et al. |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali et al. |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,433,776 B2 | 10/2019 | Al-Ali |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali |
| 10,456,038 B2 | 10/2019 | Lamego et al. |
| 10,463,284 B2 | 11/2019 | Al-Ali et al. |
| 10,463,340 B2 | 11/2019 | Telfort et al. |
| 10,470,695 B2 | 11/2019 | Al-Ali |
| 10,471,159 B1 | 11/2019 | Lapotko et al. |
| 10,478,107 B2 | 11/2019 | Kiani et al. |
| 10,503,379 B2 | 12/2019 | Al-Ali et al. |
| 10,505,311 B2 | 12/2019 | Al-Ali et al. |
| 10,512,436 B2 | 12/2019 | Muhsin et al. |
| 10,524,706 B2 | 1/2020 | Telfort et al. |
| 10,524,738 B2 | 1/2020 | Olsen |
| 10,531,811 B2 | 1/2020 | Al-Ali et al. |
| 10,531,819 B2 | 1/2020 | Diab et al. |
| 10,531,835 B2 | 1/2020 | Al-Ali et al. |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,548,561 B2 | 2/2020 | Telfort et al. |
| 10,555,678 B2 | 2/2020 | Dalvi et al. |
| 10,568,514 B2 | 2/2020 | Wojtczuk et al. |
| 10,568,553 B2 | 2/2020 | O'Neil et al. |
| RE47,882 E | 3/2020 | Al-Ali |
| 10,575,779 B2 | 3/2020 | Poeze et al. |
| 10,582,886 B2 | 3/2020 | Poeze et al. |
| 10,588,518 B2 | 3/2020 | Kiani |
| 10,588,553 B2 | 3/2020 | Poeze et al. |
| 10,588,556 B2 | 3/2020 | Kiani et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |

(56) References Cited

U.S. PATENT DOCUMENTS

| | | |
|---|---|---|
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0109600 A1* | 8/2002 | Mault .............. A61B 5/1112 340/573.1 |
| 2002/0133080 A1 | 9/2002 | Apruzzese et al. |
| 2002/0168958 A1* | 11/2002 | Ford .............. H04W 4/90 455/404.1 |
| 2003/0013975 A1 | 1/2003 | Kiani |
| 2003/0018243 A1 | 1/2003 | Gerhardt et al. |
| 2003/0036923 A1 | 2/2003 | Waldon et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0102931 A1* | 5/2004 | Ellis .............. A61B 5/1038 702/188 |
| 2004/0106163 A1 | 6/2004 | Workman, Jr. et al. |
| 2004/0117207 A1 | 6/2004 | Brown |
| 2004/0117208 A1 | 6/2004 | Brown |
| 2004/0117209 A1 | 6/2004 | Brown |
| 2004/0117210 A1 | 6/2004 | Brown |
| 2004/0138539 A1 | 7/2004 | Jay et al. |
| 2004/0147034 A1 | 7/2004 | Gore et al. |
| 2004/0199409 A1 | 10/2004 | Brown |
| 2004/0243435 A1 | 12/2004 | Williams |
| 2005/0033127 A1 | 2/2005 | Ciurczak et al. |
| 2005/0054907 A1 | 3/2005 | Page et al. |
| 2005/0055276 A1 | 3/2005 | Kiani et al. |
| 2005/0065464 A1 | 3/2005 | Talbot et al. |
| 2005/0228244 A1 | 10/2005 | Banet |
| 2005/0234317 A1 | 10/2005 | Kiani |
| 2005/0277872 A1 | 12/2005 | Colby et al. |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0224057 A1 | 10/2006 | Burd et al. |
| 2006/0258918 A1 | 11/2006 | Burd et al. |
| 2006/0281982 A1 | 12/2006 | Grata et al. |
| 2007/0004975 A1 | 1/2007 | Zribi et al. |
| 2007/0033074 A1 | 2/2007 | Nitzan et al. |
| 2007/0073116 A1 | 3/2007 | Kiani et al. |
| 2007/0123759 A1 | 5/2007 | Grata et al. |
| 2007/0167850 A1* | 7/2007 | Russell .............. G08B 21/0453 600/513 |
| 2007/0180140 A1 | 8/2007 | Welch et al. |
| 2007/0208241 A1 | 9/2007 | Drucker |
| 2007/0244377 A1 | 10/2007 | Cozad et al. |
| 2007/0265533 A1* | 11/2007 | Tran .............. A61B 5/021 600/481 |
| 2007/0273504 A1* | 11/2007 | Tran .............. A61B 5/0022 340/539.12 |
| 2007/0276270 A1* | 11/2007 | Tran .............. A61B 5/0022 600/508 |
| 2007/0282478 A1 | 12/2007 | Al-Ali et al. |
| 2008/0001735 A1* | 1/2008 | Tran .............. G06F 19/3418 340/539.22 |
| 2008/0064965 A1 | 3/2008 | Jay et al. |
| 2008/0094228 A1 | 4/2008 | Welch et al. |
| 2008/0146900 A1 | 6/2008 | Andrews et al. |
| 2008/0183060 A1 | 7/2008 | Steil et al. |
| 2008/0200782 A1 | 8/2008 | Planman et al. |
| 2008/0214912 A1 | 9/2008 | Cano |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0227876 A1* | 9/2009 | Tran .............. A61B 5/0022 600/483 |
| 2009/0243878 A1* | 10/2009 | Ricordi .............. G08B 25/016 340/870.16 |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0056876 A1* | 3/2010 | Ellis .............. A61B 5/1038 600/300 |
| 2010/0099964 A1 | 4/2010 | O'Reilly et al. |
| 2010/0190479 A1* | 7/2010 | Scott .............. G06F 40/58 455/414.1 |
| 2010/0234718 A1 | 9/2010 | Sampath et al. |
| 2010/0270257 A1 | 10/2010 | Wachman et al. |
| 2010/0331651 A1 | 12/2010 | Groll |
| 2011/0001605 A1 | 1/2011 | Kiani et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0123231 A1 | 5/2012 | O'Reilly |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |

(56) References Cited

U.S. PATENT DOCUMENTS

| | | |
|---|---|---|
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171146 A1 | 6/2014 | Ma et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0173671 A1 | 6/2015 | Paalasmaa et al. |
| 2015/0196237 A1 | 7/2015 | Lamego |
| 2015/0196249 A1 | 7/2015 | Brown et al. |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0255001 A1 | 9/2015 | Haughay et al. |
| 2015/0257689 A1 | 9/2015 | Al-Ali et al. |
| 2015/0272514 A1 | 10/2015 | Kiani et al. |
| 2015/0281424 A1 | 10/2015 | Vock et al. |
| 2015/0318100 A1 | 11/2015 | Rothkopf et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0019360 A1 | 1/2016 | Pahwa et al. |
| 2016/0023245 A1 | 1/2016 | Zadesky et al. |
| 2016/0029932 A1 | 2/2016 | Al-Ali |
| 2016/0038045 A1 | 2/2016 | Shapiro |
| 2016/0045118 A1 | 2/2016 | Kiani |
| 2016/0051157 A1 | 2/2016 | Waydo |
| 2016/0051158 A1 | 2/2016 | Silva |
| 2016/0051205 A1 | 2/2016 | Al-Ali et al. |
| 2016/0058302 A1 | 3/2016 | Raghuram et al. |
| 2016/0058309 A1 | 3/2016 | Han |
| 2016/0058312 A1 | 3/2016 | Han et al. |
| 2016/0058338 A1 | 3/2016 | Schurman et al. |
| 2016/0058347 A1 | 3/2016 | Reichgott et al. |
| 2016/0058356 A1 | 3/2016 | Raghuram et al. |
| 2016/0058370 A1 | 3/2016 | Raghuram et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0071392 A1 | 3/2016 | Hankey et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0154950 A1 | 6/2016 | Nakajima et al. |
| 2016/0157780 A1 | 6/2016 | Rimminen et al. |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0213309 A1 | 7/2016 | Sannholm et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0256058 A1 | 9/2016 | Pham et al. |
| 2016/0256082 A1 | 9/2016 | Ely et al. |
| 2016/0267238 A1 | 9/2016 | Nag |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287181 A1 | 10/2016 | Han et al. |
| 2016/0287786 A1 | 10/2016 | Kiani |
| 2016/0296169 A1 | 10/2016 | McHale et al. |
| 2016/0296173 A1 | 10/2016 | Culbert |
| 2016/0296174 A1 | 10/2016 | Isikman et al. |
| 2016/0310027 A1 | 10/2016 | Han |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2016/0378069 A1 | 12/2016 | Rothkopf |
| 2016/0378071 A1 | 12/2016 | Rothkopf |
| 2017/0007134 A1 | 1/2017 | Al-Ali et al. |

(56) References Cited

U.S. PATENT DOCUMENTS

| | | |
|---|---|---|
| 2017/0007183 A1 | 1/2017 | Dusan et al. |
| 2017/0007190 A1 | 1/2017 | Al-Ali et al. |
| 2017/0007198 A1 | 1/2017 | Al-Ali et al. |
| 2017/0010858 A1 | 1/2017 | Prest et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0074897 A1 | 3/2017 | Mermel et al. |
| 2017/0079594 A1 | 3/2017 | Telfort et al. |
| 2017/0084133 A1 | 3/2017 | Cardinali et al. |
| 2017/0086689 A1 | 3/2017 | Shui et al. |
| 2017/0086723 A1 | 3/2017 | Al-Ali et al. |
| 2017/0086742 A1 | 3/2017 | Harrison-Noonan et al. |
| 2017/0086743 A1 | 3/2017 | Bushnell et al. |
| 2017/0094450 A1 | 3/2017 | Tu et al. |
| 2017/0143281 A1 | 5/2017 | Olsen |
| 2017/0147774 A1 | 5/2017 | Kiani |
| 2017/0164884 A1 | 6/2017 | Culbert et al. |
| 2017/0173632 A1 | 6/2017 | Al-Ali |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0248446 A1 | 8/2017 | Gowreesunker et al. |
| 2017/0251974 A1 | 9/2017 | Shreim et al. |
| 2017/0258403 A1 | 9/2017 | Abdul-Hafiz et al. |
| 2017/0273619 A1 | 9/2017 | Alvarado et al. |
| 2017/0281024 A1 | 10/2017 | Narasimhan et al. |
| 2017/0293727 A1 | 10/2017 | Klaassen et al. |
| 2017/0311891 A1 | 11/2017 | Kiani et al. |
| 2017/0325698 A1 | 11/2017 | Allec et al. |
| 2017/0325744 A1 | 11/2017 | Allec et al. |
| 2017/0340209 A1 | 11/2017 | Klaassen et al. |
| 2017/0340219 A1 | 11/2017 | Sullivan et al. |
| 2017/0340293 A1 | 11/2017 | Al-Ali et al. |
| 2017/0347885 A1 | 12/2017 | Tan et al. |
| 2017/0354332 A1 | 12/2017 | Lamego |
| 2017/0354795 A1 | 12/2017 | Blahnik et al. |
| 2017/0358239 A1 | 12/2017 | Arney et al. |
| 2017/0358240 A1 | 12/2017 | Blahnik et al. |
| 2017/0358242 A1 | 12/2017 | Thompson et al. |
| 2017/0360306 A1 | 12/2017 | Narasimhan et al. |
| 2017/0366657 A1 | 12/2017 | Thompson et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0014781 A1 | 1/2018 | Clavelle et al. |
| 2018/0025287 A1 | 1/2018 | Mathew et al. |
| 2018/0056129 A1 | 1/2018 | Narasimha Rao et al. |
| 2018/0042556 A1 | 2/2018 | Shahparnia et al. |
| 2018/0049694 A1 | 2/2018 | Singh Alvarado et al. |
| 2018/0050235 A1 | 2/2018 | Tan et al. |
| 2018/0055375 A1 | 3/2018 | Martinez et al. |
| 2018/0055390 A1 | 3/2018 | Kiani et al. |
| 2018/0055439 A1 | 3/2018 | Pham et al. |
| 2018/0064381 A1 | 3/2018 | Shakespeare et al. |
| 2018/0070867 A1 | 3/2018 | Smith et al. |
| 2018/0078151 A1 | 3/2018 | Allec et al. |
| 2018/0078182 A1 | 3/2018 | Chen et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110469 A1 | 4/2018 | Maani et al. |
| 2018/0125368 A1 | 5/2018 | Lamego et al. |
| 2018/0125430 A1 | 5/2018 | Al-Ali et al. |
| 2018/0132769 A1 | 5/2018 | Weber et al. |
| 2018/0146901 A1 | 5/2018 | Al-Ali et al. |
| 2018/0146902 A1 | 5/2018 | Kiani et al. |
| 2018/0153418 A1 | 6/2018 | Sullivan et al. |
| 2018/0153442 A1 | 6/2018 | Eckerbom et al. |
| 2018/0153446 A1 | 6/2018 | Kiani |
| 2018/0153448 A1 | 6/2018 | Weber et al. |
| 2018/0164853 A1 | 6/2018 | Myers et al. |
| 2018/0168491 A1 | 6/2018 | Al-Ali et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0196514 A1 | 7/2018 | Allec et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0228414 A1 | 8/2018 | Shao et al. |
| 2018/0238718 A1 | 8/2018 | Dalvi |
| 2018/0238734 A1 | 8/2018 | Hotelling et al. |
| 2018/0242853 A1 | 8/2018 | Al-Ali |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0279956 A1 | 10/2018 | Waydo et al. |
| 2018/0285094 A1 | 10/2018 | Housel et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0015023 A1 | 1/2019 | Monfre |
| 2019/0029574 A1 | 1/2019 | Schurman et al. |
| 2019/0029578 A1 | 1/2019 | Al-Ali et al. |
| 2019/0058280 A1 | 2/2019 | Al-Ali et al. |
| 2019/0069813 A1 | 3/2019 | Al-Ali |
| 2019/0076028 A1 | 3/2019 | Al-Ali et al. |
| 2019/0082979 A1 | 3/2019 | Al-Ali et al. |
| 2019/0090760 A1 | 3/2019 | Kinast et al. |
| 2019/0090764 A1 | 3/2019 | Al-Ali |
| 2019/0117070 A1 | 4/2019 | Muhsin et al. |
| 2019/0117139 A1 | 4/2019 | Al-Ali et al. |
| 2019/0117141 A1 | 4/2019 | Al-Ali |
| 2019/0117930 A1 | 4/2019 | Al-Ali |
| 2019/0122762 A1 | 4/2019 | Al-Ali et al. |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |

(56) References Cited

U.S. PATENT DOCUMENTS

| | | |
|---|---|---|
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali |
| 2019/0357813 A1 | 11/2019 | Poeze et al. |
| 2019/0357823 A1 | 11/2019 | Reichgott et al. |
| 2019/0357824 A1 | 11/2019 | Al-Ali |
| 2019/0358524 A1 | 11/2019 | Kiani |
| 2019/0365294 A1 | 12/2019 | Poeze et al. |
| 2019/0365295 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000415 A1 | 1/2020 | Barker et al. |
| 2020/0015716 A1 | 1/2020 | Poeze et al. |
| 2020/0021930 A1 | 1/2020 | Iswanto et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060591 A1 | 2/2020 | Diab et al. |
| 2020/0060628 A1 | 2/2020 | Al-Ali et al. |
| 2020/0060629 A1 | 2/2020 | Muhsin et al. |
| 2020/0060869 A1 | 2/2020 | Telfort et al. |
| 2020/0074819 A1 | 3/2020 | Muhsin et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |

OTHER PUBLICATIONS

US 9,579,050 B2, 02/2017, Al-Ali (withdrawn)

"Apple—Downloads—Home & Learning—1-2Tracker" at http://www.apple.com/downloads/macosx/home_learning/12tracker.html, accessed on Feb. 16, 2009.

"Apple—Downloads—Home & Learning—Diabetes Logbook X" at http://www.apple.com/downloads/macosx/home_learning/diabeteslogbookx.html, accessed on Feb. 16, 2009.

"Apple—Downloads—Home & Learning—HealthEngage Diabetes" at http://www.apple.com/downloads/macosx/home_learning/healthengagediabetes.html, accessed on Feb. 16, 2009.

"Apple—Web apps—Diabetes Headline News" at http://www.apple.com/webapps/news/diabetesheadlinenews.html, accessed on Feb. 19, 2009.

"iPhone and iPod Touch Application List >> A Low GI Diet—Glycemic Index Search" at http://iphoneapplicationlist.com/2009/02/02/a-low-gi-diet-glycemic-index-search/, accessed on Feb. 16, 2009.

"Tech, Medical Device Cos Target Wireless Diabetes Monitoring," Roger Cheng and Jon Kamp, Dow Jones Newswires, http://online.wsj.com/article/BT-CO-20090930-712994.html, Sep. 30, 2009.

"Total Hemoglobin" at http://www.masimo.com/hemoglobin/index.html, accessed on Jun. 29, 2009.

\* cited by examiner

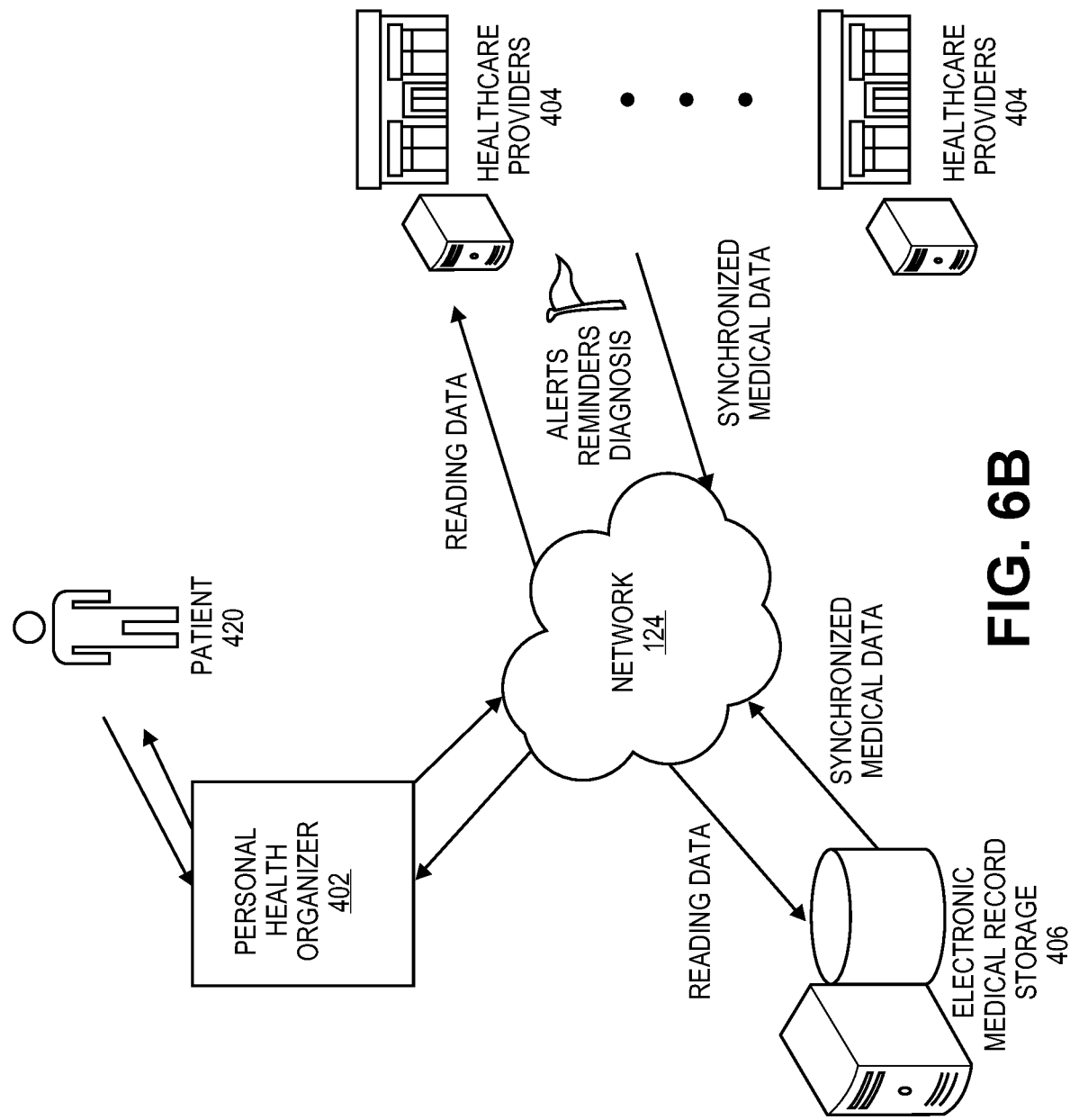

SYSTEM FOR MONITORING A PHYSIOLOGICAL PARAMETER OF A USER

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure relates to the field of patient monitoring devices. More specifically, the disclosure relates to portable and handheld personal health organizers that are adapted to be coupled with patient monitors that measure physiological characteristics such as blood glucose level, total hemoglobin, $SpO_2$, methemoglobin, carboxyhemoglobin, and the like.

Description of the Related Art

Caregivers often employ patient monitoring systems or devices, such as pulse oximeters, capnographs, blood pressure cuffs, and the like, for convenient spot checking and even continuous monitoring of physiological characteristics of a patient. Patient monitoring systems generally include one or more sensors applied to a patient, a monitoring device, and one or more cables connecting the one or more sensors to the monitoring device.

Portability of these monitoring systems is advantageous for a number of reasons. For example, portable devices provide the patient with mobility and provide the caregiver the option of including the monitoring device when transporting patients from one setting to another. Also, caregivers often transport patients from an ambulance to a hospital emergency room, and between surgical, intensive care, and recovery settings. As another example, portable devices can also provide the patient the capability of using the monitoring systems at home or the office.

An example of a patient monitoring device is a glucometer, which is used in a procedure for measuring glucose concentration in the blood. Glucometers are a key element of home blood glucose monitoring by people with diabetes mellitus or prone to hypoglycemia. A glucometer typically provides a numerical readout of the patient's glucose level. Other monitor devices may measure physiological characteristics such as total hemoglobin, $SpO_2$, methemoglobin, carboxyhemoglobin, etc.

For many conventional patient monitoring devices such as pulse oximeters or glucometers, separate monitoring devices may be needed to measure the oxygen and glucose level saturations. Viewing and analyzing different physiological characteristics would also require separate devices. Moreover, conventional patient monitoring devices are limited to the specialized functions provided by the individual devices, which often include limited data analysis or synchronization capabilities.

SUMMARY OF THE DISCLOSURE

Embodiments of the present disclosure provide a portable health organizer that enables patients and healthcare personnel to manage health data, and in particular, physiological reading data from one or more health data collection devices such as a glucometer or pulse oximeter. In an embodiment, the personal health organizer is a dedicated portable device that is adapted to retrieve reading data from a health data collection device, which is a noninvasive device in an embodiment and an invasive device in another embodiment.

In another embodiment, the personal health organizer is a software module/platform that is configured to be executed on a general purpose computing device such as a personal computer, a laptop, a mobile phone, a mobile computer, and a wristwatch computer. The general purpose computer device is directed by the personal health organizer software module/platform to collect or receive data from either an invasive or non-invasive health data collection device. Another embodiment is a personal health organizer device that includes an integrated health data collection module that is configured to receive physiological data reading from a sensor. The personal health organizer can measure various physiological reading data invasively or non-invasively through a sensor connected through a sensor port in an embodiment.

In an embodiment, the personal health organizer provides seamless integration of the reading data with the patient's existing medical data and with a number of software applications that help a patient manages his or her health. For example, the physiological reading data, e.g., blood glucose, total hemoglobin, $SpO_2$, methemoglobin, carboxyhemoglobin, can be tracked over a time period so the patient is reminded to take medication and/or perform a new reading. The reminders can be customized or calculated based on prior medical history and/or personal information such as age and gender stored in the personal health organizer. As another example, the reading data can also be forwarded to healthcare providers such as physicians and pharmacies so they can provide feedback to the patient. The personal health organizer can also trigger alerts if the reading data indicate an abnormal level that requires medical attention.

In addition to the forgoing, embodiments of the present disclosure also provide electronic medical record (EMR) integration in conjunction with support for medical record synchronization across networked locations (e.g. via a cloud computing network). Medical data (including reading data and other patient-entered data such as medication schedule and activity/food in-take logs) from the personal health organizer device are automatically synchronized with the corresponding records located at a remote entity (e.g. in a centralized EMR storage or at the healthcare providers' data storage). For example, newly obtained reading data can be synchronized with a shared, synchronized calendar so that both the physician and the patient user can adjust an appointment if the reading requires a change in the appointment schedule. As another example, prescription information can be synchronized so that reimbursements can be handled automatically when the user finishes a current prescription and purchases a new refill. In another example, the personal health organizer can initiate the prescription refill process after verifying drug interaction and consent of the user and the physician.

In other embodiments, the personal health organizer includes an accelerometer that detects user motion and the motion can assist in the collection of and/or display of medical/reading data. For example, the accelerometer can detect a user's intent to use the device via touch/motion and automatically start the collection of data when the user places his or her finger into a sensor associated with a health collection data device. In another example, the personal health organizer can begin health data collection once the user places his or her finger into a sensor associated with a health collection data device and/or provides a gesture via a touch-screen input associated with the personal health organizer. In yet another example, the personal health organizer begins the data collection when the user places a finger into the sensor. The LEDs and photo diodes in the sensor can detect the presence of the finger and initiate data collection. The presence of a finger can be determined, for example, by determining when there is a significant reduction in detected light. Such a reduction in detected light can indicate the presence of a finger and start the data collection process.

In other embodiments, the personal health organizer includes a number of health education and gaming modules designed to educate the user on health management and motivate the user toward a healthier lifestyle. The educational and gaming content can be customized based on the user's current reading data. For example, a tree icon indicative of the user's health can be displayed on the personal health organizer, with the health of the tree corresponding to the recent readings obtained directly by the personal health organizer through a connected sensor or through an associated health data collection device.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 6B illustrates the transfer and synchronization of reading data and medical data in accordance with one embodiment.

DETAILED DESCRIPTION OF PREFERRED AND ALTERNATIVE EMBODIMENTS

Embodiments of the invention will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention can include several novel features, no single one of which is solely responsible for its desirable attributes or which is essential to practicing the inventions herein described.

Systems, methods, and computer-readable media are disclosed for obtaining and analyzing medical data from a medical device or a data server. More specifically, systems, methods, and computer readable media are disclosed for enabling a portable device to obtain and analyze medical data from a health data collection device, such as a glucometer.

Figure 1A:
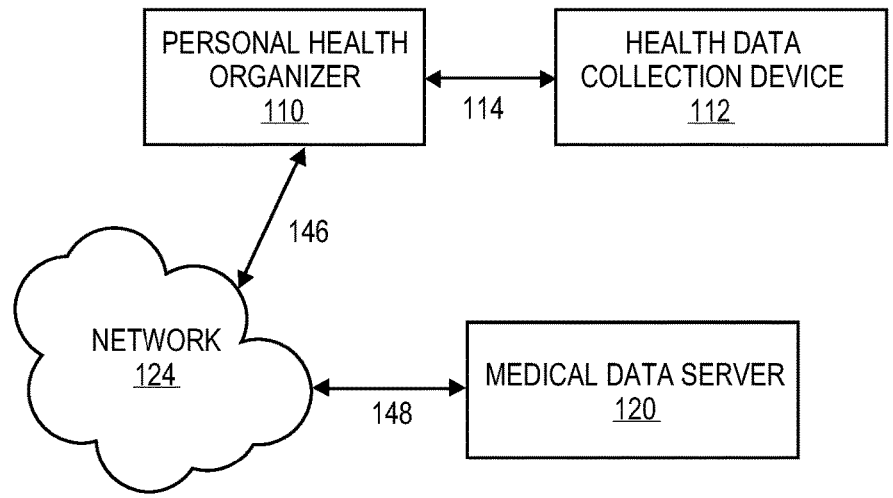
FIGS. 1A and 1B illustrate an embodiment of a personal health organizer.
Figure 1B:
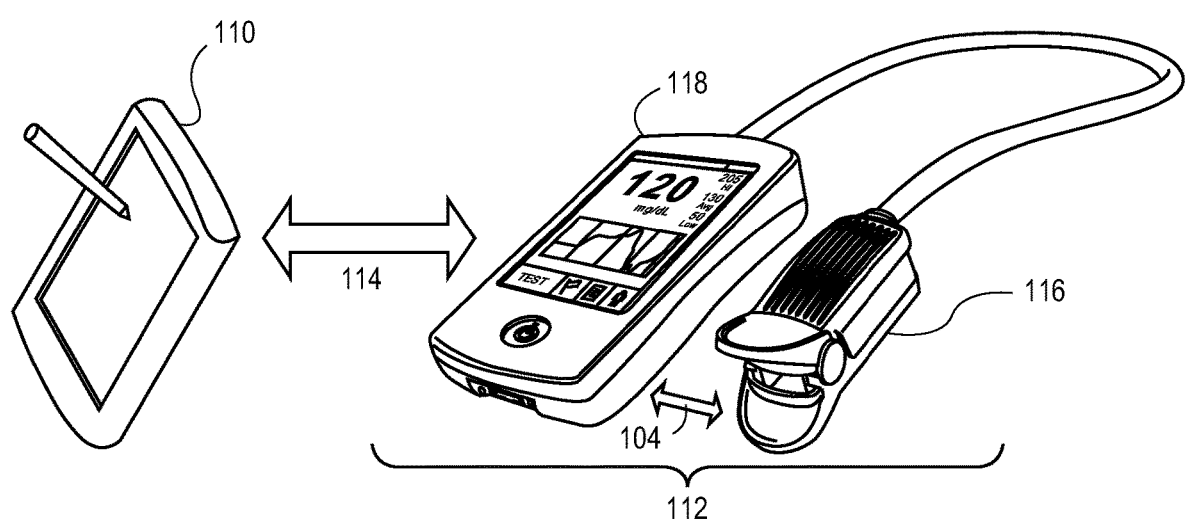
Figure 2A:
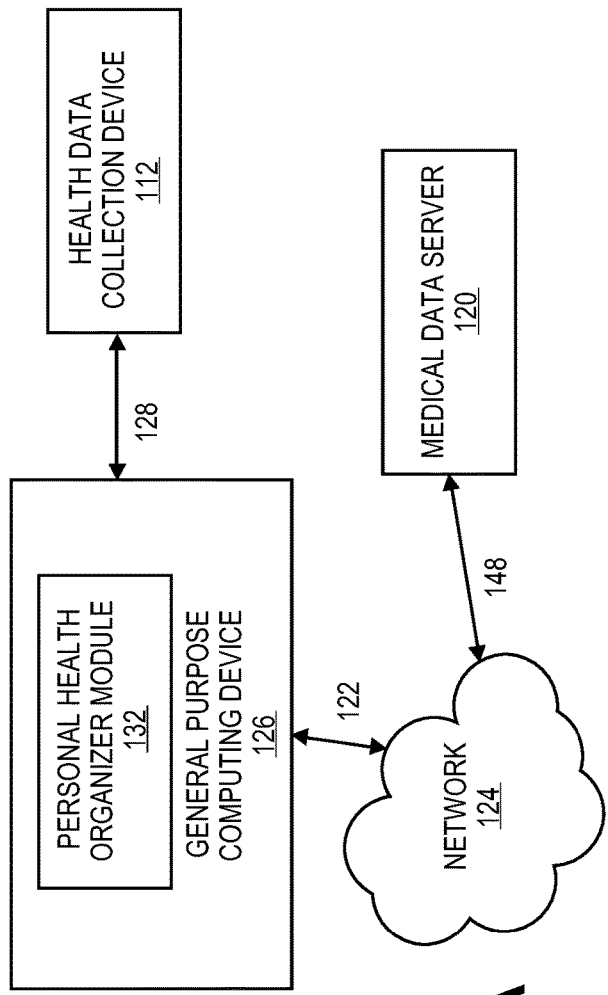
FIGS. 2A and 2B illustrate another embodiment of a personal health organizer.
Figure 2B:
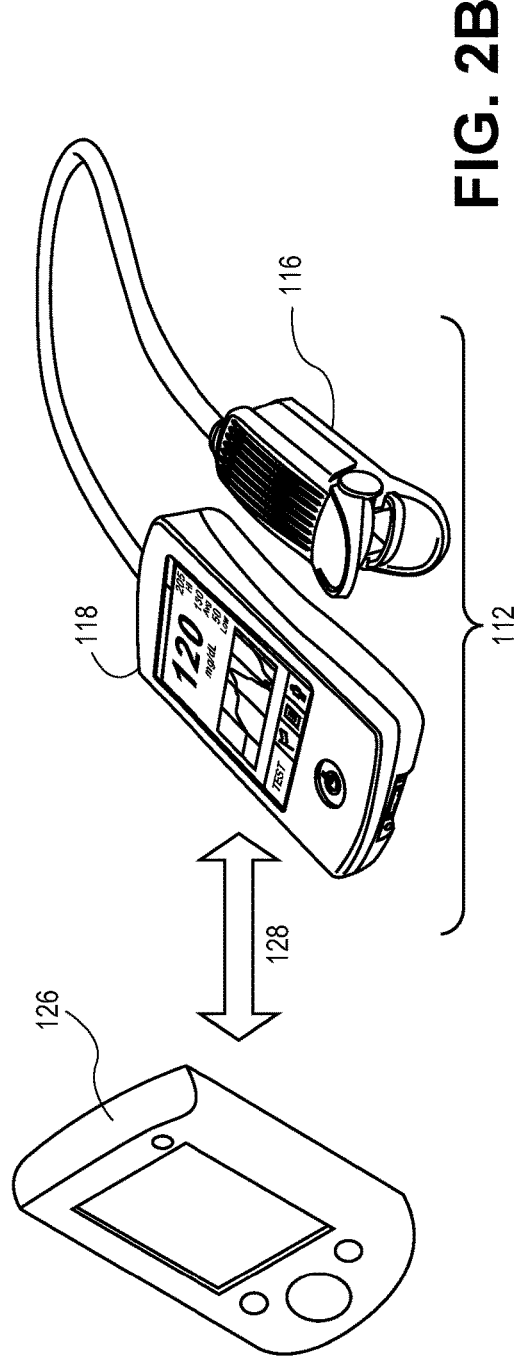
Figure 3A:
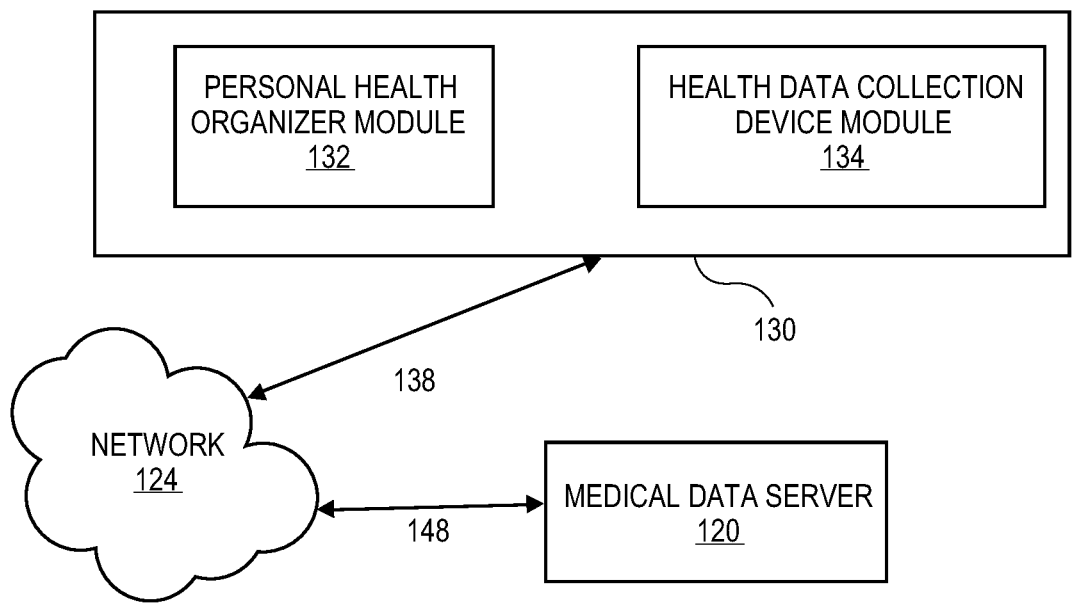
FIGS. 3A and 3B illustrate yet another embodiment of a personal health organizer.
Figure 3B:
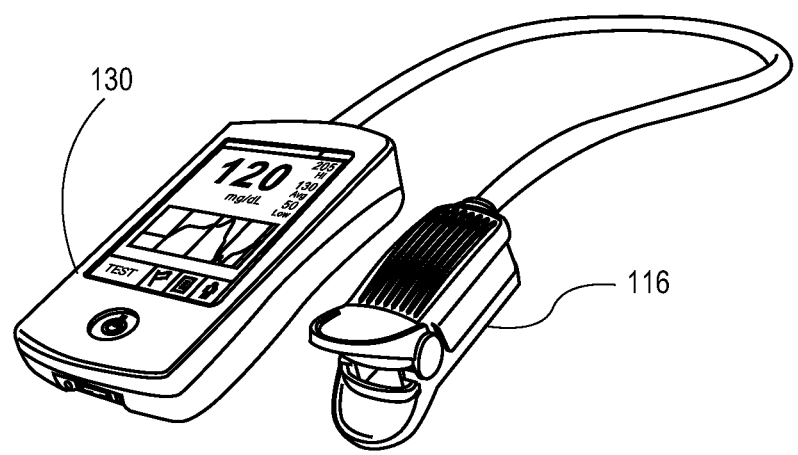

FIGS. 1A-1B, 2A-2B, and 3A-3B illustrate three primary embodiments of the personal health organizer. First, FIGS. 1A and 1B depict a dedicated portable personal health organizer device that is configured to receive data from a health data collection device such as a glucometer. In an embodiment, the personal health organizer is configured to analyze data from the collection device, manage the collected data, and use the collected data to assist the patient in managing his or her personal healthcare. For example, the collected data can be used to schedule reminders for the patient to visit his or her physician or pharmacist. Second, FIGS. 2A and 2B depict a general purpose computing device configured to execute a personal health organizer software module, with the computing device further configured to receive data from a health data collection device such as a glucometer. The general purpose computing device can be a mobile computing device with its own operating system and software, and has installed upon it the personal health organizer software module configured to perform tasks that are substantially similar to those performed by the dedicated personal health organizer depicted in FIGS. 1A and 1B. Finally, FIGS. 3A and 3B depict a device that integrates a personal health organizer software module with a health data collection device module, with the collection device module coupled with hardware to perform tasks of health data collection such as those performed by a glucometer or other patient monitoring device described above. Each of these primary embodiments will be described in further detail below.

Personal Health Organizer as a Dedicated Portable Device

FIG. 1A shows a personal health organizer 110 as a device configured for analyzing data collected by a health data collection device 112. As shown in FIG. 1A, the personal health organizer 110 can be connected to the health data collection device 112 via a communications link 114. The communications link 114 can be a wired or wireless connection adapted to transfer data between the two devices. Examples of wired connections include USB, serial, and parallel and examples of wireless connections include Bluetooth®, Wi-Fi, WiMAX, Wireless USB, and ZIGBEE. In various embodiments, the health data collection device 112 is configured to collect physiological data from a patient invasively or non-invasively. The health data collection device 112 can be a glucometer, a pulse oximeter, monitor devices that measure total hemoglobin, $SpO_2$, methemoglobin, carboxyhemoglobin, and the like. Example portable non-invasive monitoring devices are disclosed in co-pending U.S. patent application Ser. No. 12/534,827, filed Aug. 3, 2009, assigned to Masimo Labs of Irvine, Calif., the Assignee of the present application, the disclosure of which is incorporated herein by reference.

The personal health organizer 110 can comprise a computing system configured to perform functional tasks of various embodiments of the invention. For example, in an embodiment, the personal health organizer 110 accesses data collected by the health data collection device 112 or stored at a medical data server 120 connected via a network 124, which can include a LAN, WAN, or the Internet. The medical data server 120 and the personal health organizer 110 can be connected to the network via communications links 146 and 148, respectively, and the communications links can include wired or wireless connections. The medical data server 120 can be a conventional, preexisting data system operated by an entity such as a hospital or an insurance company.

In the embodiment depicted in FIG. 1B, the health data collection device 112 includes a finger clip sensor 116 connected to a monitor 118 via a cable. Moreover, the monitor 118 can advantageously includes electronic processing, signal processing, and data storage devices capable of receiving signal data from the sensor 116, processing the signal data to determine one or more output measurement values indicative of one or more physiological parameters of a monitored patient, and displaying the measurement values, trends of the measurement values, combinations of measurement values, and the like. Alternatively, in an embodiment, the personal health organizer 110 includes a sensor port that allows for a sensor such as the sensor 116 to be connected directly to the personal health organizer 110, and in that embodiment the personal health organizer 110 includes components and devices for processing the signal data from the sensor 116.

The monitor 118 can also include other components, such as a speaker, a power button, removable storage or memory (e.g., a flash card slot), an AC or DC power port, and one or more network interfaces, such as a universal serial bus (USB) interface, an Ethernet port, or a wireless port. These interfaces and ports can be used by the monitor 118 in one embodiment to communicate with the sensor 116 via a communication link 104, which may include various types of communication protocols and links as described above with respect to the communication link 114. For example, the monitor 118 can include a display that can indicate a measurement for glucose, for example, in mg/dL. Other analytes and forms of display can also appear on the monitor 118.

In addition, although a single sensor with a single monitor 118 is shown, different combinations of sensors and device pairings can be implemented. For example, multiple sensors can be provided for a plurality of differing patient types or measurement sites or even patient fingers. The sensor 116 can also connect to the monitor 118 wirelessly. Alternatively, the sensor 116 and the monitor 118 can be integrated into a single unit. A skilled artisan would appreciate that many other monitoring device configurations can be used as well.

Personal Health Organizer as a Software Module

FIG. 2A depicts another embodiment with a personal health organizer software module 132 executed on a general purpose computing device 126, with the computing device 126 coupled with the health data collection device 112 via a communications link 128. The communications link 128 can be a wired or wireless connection adapted to transfer data between the two devices. The personal health organizer module 132 can be an executable program on an operating system of a device such as a mobile phone, a personal digital assistant, a portable music player, an electronic book reader, a netbook, a TV media center, and a laptop or desktop computer. For example, the personal health organizer module 132 can be an application that is executed on the operating system of a mobile phone such as the iPhone manufactured by Apple, Inc., a Blackberry device manufactured by Research In Motion, Inc., the Pre manufactured by Palm, Inc, or a mobile device manufactured by HTC, Nokia, or Motorola, etc. In an embodiment, the personal health organizer software module 132 is configured to perform tasks that are substantially similar to those performed by the dedicated personal health organizer depicted in FIG. 1A. In an embodiment, the computing device 126 is connected to the network 124 via a communications link 122, which can be a wired or wireless connection. As with FIG. 1A, the computing device 126 can be connected to the medical data server 120 via the network 124.

As shown in FIG. 2B, the general computing device 126 can be coupled with the health data collection device 112, with the monitor 118 and sensor 116 as described above. In the embodiments shown in FIGS. 1A, 1B, 2A, and 2B, the communication and/or I/O interfaces of the health data collection device 112 can be used to connect to personal health organizer 110 or 126. For example, the USB interface could be used to connect the monitor 118 to a USB port of the personal health organizer 110 or 126. As another example, the wireless port of the health data collection device 112 could be used to communicate with the personal health organizer via a wireless link, such as an RF or infrared link or a Bluetooth® link. A skilled artisan will appreciate that a variety of other configurations and communication mechanisms are possible. For example, in an embodiment, general purpose computer device 126 includes a sensor port that allows for a sensor such as the sensor 116 to be connected directly to the general purpose computer device 126, and in that embodiment the general purpose computer device 126 includes components and devices for processing the signal data from the sensor 116. In another embodiment, the sensor 116 can be connected wirelessly to the general purpose computer device 126 through one or more known wireless connection protocols such as Bluetooth®. A skilled artisan will also appreciate that connecting the monitor 118 to the personal health organizer can allow the personal health organizer to collect, store, or analyze the output measurement values produced by the monitor 118.

Integrated Device with Personal Health Organizer and Health Data Collection Modules FIG. 3A depicts another embodiment with a personal health organizer software module 132 executed on a computing device 130 that is integrated with a health data collection device module 134. In an embodiment, the health data collection device module 134 is configured to collect physiological data such as glucose reading and other physiological parameters. In an embodiment, the health data collection device module 134 includes components and devices for processing the signal data from the sensor 116. As shown in FIG. 3B, the integrated device 130 can include a monitor display and a sensor 116. The monitor display can provide for display for both the personal health organizer software module 132 and the health data collection device module 134. In an embodiment, the sensor 116 can be further integrated into the integrated device 130. In another embodiment, the wire connecting the sensor 116 to the integrated device 130 can be retractable or detachable so that the sensor 116 can be housed within the integrated device 130 or elsewhere when the sensor 116 is not in use. In the detachable embodiment, the integrated device 130 includes a sensor port that allows for the sensor 116 to be connected directly to the integrated device 130 through one or more known connection/communication protocols including USB and Ethernet. The sensor 116 can also connect wirelessly to the integrated device 130.

In one or more embodiments, the personal health organizer 110, 126 or 130 can be covered by a water-proof case (e.g. a case that can withstand water pressure up to 300M in depth). In an embodiment, the sensor 116 is either detached from the personal health organizer device or integrated into the personal health organizer within the water-proof case. The case can allow, for example, divers to use the personal health organizer under water.

Although a single personal health organizer is depicted in FIGS. 1A-3B, many different personal health organizers, monitoring devices, or sensors that operate as described above can be provided. In addition, multiple distinct healthcare entities and systems can communicate with a personal health organizer and its associated monitoring device and/or sensor. This can include corporate two-way interaction of data hubs such as Google Health, Microsoft Health Vault, and hubs maintained by WellPoint or other insurers. One skilled in the art will appreciate that any number of patients or healthcare professionals can be provided access to the personal health organizer 110, 126, or 130 or the data server 120.

Personal Health Organizer Components—General

Figure 4:
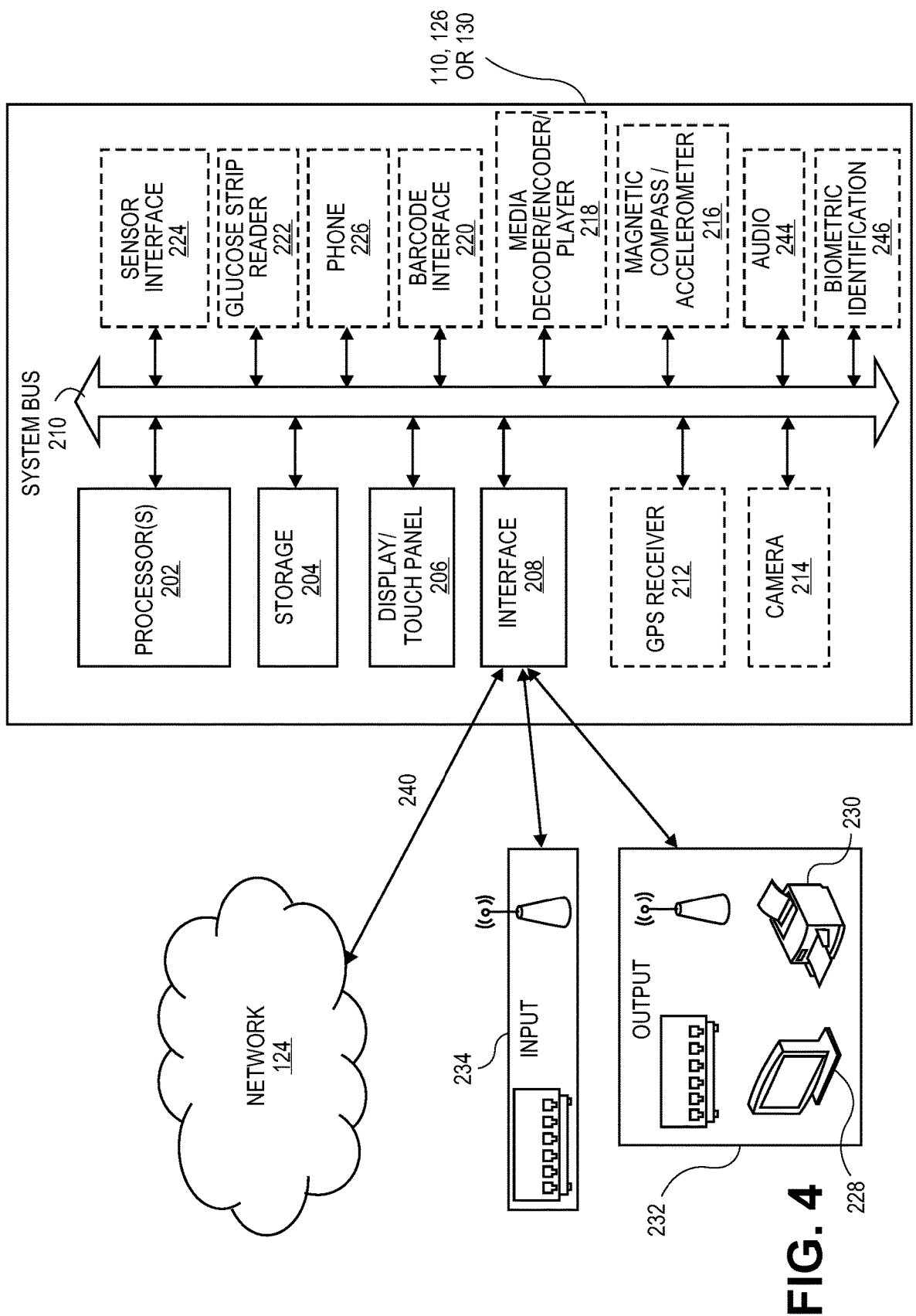
FIG. 4 is a block diagram that illustrates the components of a personal health organizer in accordance with one embodiment.

FIG. 4 illustrates in more detail components of an example personal health organizer 110, general computing device 126 (with a personal health organizer module 132) or integrated device 130 in accordance with various embodiments (hereinafter referred to as "personal health organizer"). In an embodiment, the components are divided into required components and optional components. In FIG. 4, the required components are illustrated in blocks with continuous lines while the optional components are illustrated in blocks with dotted lines.

As illustrated in FIG. 4, various embodiments of the personal health organizer include one or more of the following components: one or more computer processor(s) 202, a storage 204, a display/touch panel 206, and an interface 208. One or more of these components can be connected together via a system bus 210. In an embodiment, the storage 204 includes (1) data storage such as a hard disk and/or removable media such as a flash drive, and/or (2) memory storage such as RAM or ROM. The processor(s) 202 can process signals received from a sensor such as the sensor 116 shown in FIGS. 1B, 2B, and 3B and derive physiological readings such as blood glucose level or other parameters from the signals. The storage 204 can include instructions or data for performing one or more methods disclosed herein. In one or more embodiments, the storage 204 includes a media card reader interface that accepts a media card such as an SD card, a microSD card, a memory stick, a CF card and the like. The portable media card can be used to store patient information and enable the personal health organizer device to be shared, with the settings and data for the individual user stored in the user's media card. The personal health organizer can also include a biometric identification module (such as a vein pattern or finger print scanner) 246 to distinguish one user from another or provide security for information stored.

In an embodiment, a personal health organizer computing platform/module 300 and related modules (shown in FIG. 5) are stored in storage 204 and executed on the processor 202. Additionally, the personal health organizer can access information including patient medical and reading data stored in storage 204 in performing methods disclosed herein.

The interface 208 can include an input 234, which can in turn include wired and wireless input connections in accordance with various protocols such USB, serial, parallel, SATA, Firewire (IEEE 1394), Bluetooth®, Wi-Fi, WiMAX, Wireless USB, ZIGBEE, etc. Although interface 208 is shown as a simple interface, multiple interfaces could be used. For example, the interface can include one or more commonly available input/output (I/O) interfaces that provide a communication interface to various external devices, connected via a wired, wireless, or combination of wired and wireless, communication link. In addition, sensor interface 224 can double as a wired interface to other connection types.

The input 234 can also accept input from an input device such as a keyboard, a mouse, a speech recognition device, a touch screen device and/or other data entering devices. In an embodiment, the user inputs information through the touch screen functionality integrated into the display/touch panel 206. The input 234 can be connected to the health data collection device 112, other medical devices, other computing devices, etc. to collect medical and/or physiological reading data that is to be processed, analyzed, and/or communicated.

In an embodiment, the interface 208 also includes a network interface 240 that can receive information over any type of network, such as a telephony-based network (e.g., PBX or POTS), a local area network (LAN), a wide area network (WAN), a dedicated intranet, and/or the Internet. The network interface 240 can include a wired interface such as an Ethernet interface or a wireless interface such as Wi-Fi or WiMAX.

The personal health organizer can be adapted to provide output information to an output 232, with the information output through wired and wireless connections in accordance with various protocols such USB, serial, parallel, SATA, Firewire, Bluetooth®, Wi-Fi, WiMAX, Wireless USB, ZIGBEE, etc. Information can also be output to an external display 228 and/or a printer 230.

As further described below, the personal health organizer can use the stored patient information to generate reports, alerts, and the like for healthcare providers. The personal health organizer can then output the medical information via the output 232 and/or send the medical information through via the network 124.

The storage 204 can store personal data associated with patients connected to the personal health organizer, such as name, address, telephone number, driver's license number, social security number, credit card account number, checking account number, age, gender, ethnicity, etc. Sensitive or personal data may be stored in an encrypted format and/or not stored on the personal health organizer. In an embodiment, the user is provided with data storage and security options and can configure the device as desired. In an embodiment, information stored on the device can be remotely wiped, for example, if the device is lost or stolen. The storage 204 can preferably also include records of reports generated for the healthcare providers (when a provider is the user) or patients, alerts generated for the healthcare providers or patients, patients associated with the healthcare providers, and requests made by the healthcare providers or patients. The storage 204 can also include the healthcare provider's or patient's membership identification ("ID") and password. The information to be stored in the storage 204 can be entered, obtained, or transmitted using the touch screen enabled display 206, the input and output 232 and 234, and/or the network interface 240.

The personal health organizer in an embodiment includes one or more of: a media decoder/encoder/player 218 for playing back music and media, a phone 226, a built-in video/still capability camera 214, a barcode interface 220, a magnetic compass/accelerometer 216, a sensor interface 224, a glucose strip reader 222, a biometric identification module (such as a retinal, vein pattern, or finger-print scanner) 246, and an audio component 244. The media player 218 can play back media such as music and video via a media center software displayed on the display 206. The camera 214 can support a document scanner that allows user to input documents and forms from healthcare providers or insurance companies. In an embodiment, the camera is paired with an optical character recognition module so that scanned medical forms can be converted into data that can be uploaded for synchronization at a server in a network (e.g. a cloud computing network) or stored on the personal health organizer device. The scanner can also enable the user to fill out a medical form and send the completed form to a healthcare provider or an insurance company. User can also photograph or scan the bar code of prescriptions and food packaging to obtain information on drug and nutrition.

The sensor interface 224 can be used to connect to a health data collection device and/or a sensor such as the sensor 116 shown in FIGS. 1A-3B to obtain reading data from the device or sensor. The glucose strip reader 222 can be used to read/scan glucose strips and obtain reading data from the strips. The barcode interface 220 can be used for distinguishing patient records in a hospital setting.

The personal health organizer can also include a GPS receiver component 212, which can determine the location of the personal health organizer. The GPS receiver component 212 can include a digital GPS receiver that can determine the location of the personal health organizer by determining coordinates, such as latitude, longitude, altimeter, etc. using conventional methods know in the art. In the case of an emergency associated with a user of the personal health organizer, emergency services or address book contacts can be contacted and location information of the user can be given by the personal health organizer using information provided by the GPS receiver component 212. In addition, the personal health organizer can be adapted to locate and discover nearby healthcare facilities and/or computing devices. For instance, the personal health organizer can determine its location as discussed above, and from knowing its location it could determine the closest hospital or pharmacy, etc. The personal health organizer can also determine what medical devices, equipment, monitors, and/or other computing devices are located near it, for example, by using the broadcast IDs of these devices (e.g. Wi-Fi SSIDs).

In an embodiment, the magnetic compass/accelerometer component 216 enables a virtual reality capability. For example, a panoramic photo can be viewed on the display 206 by tilting/rotating the device, where the device updates the current viewing angle of the picture using the 3D acceleration vector from the accelerometer and the direction from the magnetic compass. In an embodiment, other accelerometer-related features include an orientation aware graphic user interface (GUI) on the display 206, whereby the GUI adjusts according to the physical orientation of the personal health organizer device. In another embodiment, the GUI provides a hospital navigational feature that can assist a user with navigating or routing through a hospital, for example, using a virtual reality depiction of the hospital. In addition, the display 206 can be configured so that a "Portrait View" is used to display numbers and a "Horizontal/Landscape" view is used to view full screen trended data (e.g. readings tracked over a period of time). Both view options can be overridden in the control menu of the personal health organizer device. While in the "trend view," in an embodiment, the user can slide the trend timeline along a horizontal axis shake of the device, which can be taken to be a user generated gesture interaction with the device. In another embodiment, the user can rapidly shake the personal health organizer device and press the power button shortly to clear the trend that is being viewed. In another embodiment, the user can control or access the scroll menu with a vertical axis shake. An icon can be displayed to show a 2D bubble level and/or a 3D bubble level to give the user feedback that the device is being used in a good orientation for use.

In yet another embodiment, while the personal health organizer device is in an "Exercise Activity Flag Mode," the physical movement of the user is measured and correlated with the user's pulse rate, with the pulse being measured by the personal health organizer or a sensor strapped to the exercising user, in order to rate the user's physical activity.

In other embodiments, the accelerometer can be used so that a three-axis tilt of the device can adjust the perspective view of numerical 3D objects, and a three-axis tilt of the device can adjust the perspective view of the graph for more information. In other embodiments, a steady rapid shake of the device can be reflected in the falling apart of screen information on the display 206 and a prompt to notify the user that heavy vibration is detected. Rapid shaking of the device during an alarm clock notification can snooze the alarm.

The personal health organizer can include a device history log in which a user voluntarily provides access to log data so the manufacturer of the personal health organizer device can determine usage frequencies of various features. The log can be anonymized so that personal medical data is blacked out, blocked, or not provided.

Personal Health Organizer Components—Accessibility Features

The personal health organizer can also include software and/or hardware support (e.g. the audio component 244) for providing a user interface for visually impaired users, including speech and command recognition. In an embodiment, the personal health organizer provides haptic (touch-based) feedback. The feedback can be provided in addition to the audible voice and tonal feedback of the device (e.g. having a vibration notification on each screen interaction to assist the user in navigating the screens).

One embodiment of the personal health organizer includes an "auto-start" feature in which, after power on, the motion sensor and sensor 116 detects if a finger is placed and held steady for a time period (e.g. two seconds) at the sensor 116. If so, the device starts the measurement and can optionally upload the result to a server. In an embodiment, the auto-start feature can be paired with audible instructions, sent via the audio component 244, to assist the user in using the device in auto-start mode.

Modules of the Personal Health Organizer

Figure 5:
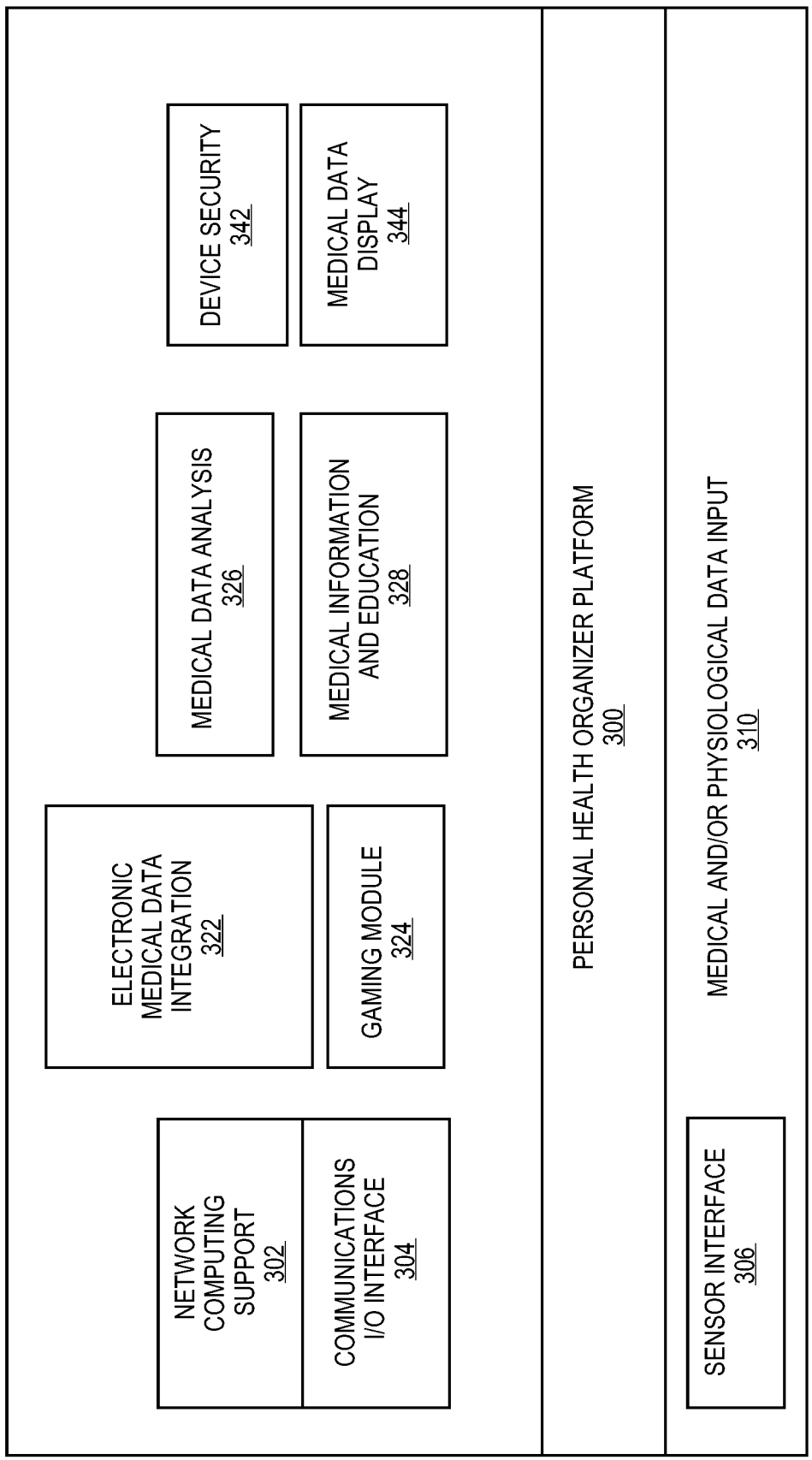
FIG. 5 is a block diagram that illustrates the modules of a personal health organizer in accordance with one embodiment.

In one or more embodiments, the personal health organizer device includes one or more modules as shown in FIG. 5. As shown, the personal health organizer device includes a medical and/or physiological data input software module 310 that supports and/or controls the receipt of medical or physiological reading data from the health data collection device 112, for example. In addition, a sensor interface module 306 can be included in the personal health organizer device to interface with various sensors. For example, in the embodiment depicted in FIGS. 3A and 3B, where the health data collection functionality is integrated into the personal health organizer device, the personal health organizer includes the sensor interface module 306 to interface with the attached sensor 116.

In an embodiment, the personal health organizer or personal health organizer module further includes a personal health organizer software platform 300 on which one or more of the following modules can be executed. In another embodiment, the modules can be executed on an operating system on a computing device apart from the personal health organizer platform 300. The modules include a network computing support module 302, a communications I/O interface module 304, an electronic medical data integration module 322, a gaming module 324, a medical data analysis module 326, a medical information and education module 328, a device security module 342, and a medical data display module 344. These modules are further described as follows.

Medical Data Analysis Module

The medical data analysis module 326, by way of example, can be used to receive medical or physiological data from the health data collection device 112 and/or the sensor 116. For example, the medical data analysis module 326 can be used to receive the measurement outputs from the monitor 118 in FIGS. 1B and 2B. As another example, the medical data analysis module 326 can be used to receive data from the sensor 116 in FIG. 3B. The medical data analysis module 326 can then analyze the data received from the sensor 116 to determine reading data and/or measurement values similar to those determined by the monitor 118.

After receiving or determining the reading data, the medical data analysis module 326 can perform analysis on the reading data. For example, the medical data analysis module 326 can determine both pre-prandial and post-prandial peak glucose levels. This analysis can help healthcare professionals know when and how to titrate medications, especially for patients who are on an insulin sliding scale coverage. As another example, the medical data analysis module 326 can determine the mean glucose levels (daily, weekly, or monthly, etc.). The medical data analysis module 326 can also determine the correlation between the hemoglobin A1c and the glucose levels over a period of time, e.g., a two to three month period. This can show how well controlled the patient's blood sugar level is based on the glucose readings from the glucometer. These functions described can be performed by the medical data analysis module 326, a sub-module, and/or a separate program on the personal health organizer.

Medical Data Analysis Module—Data Tracking

In addition to receiving medical data, the medical data analysis module 326 can be configured to send collected or stored medical data to interested parties using the network computing support module 302 and/or the communications I/O interface module 304. For example, the medical data analysis module 326 can send a digital copy of a user's entire medical record, proof of health insurance, etc. to interested parties, such as a physician office. Medical data including current and past readings, reading trends, analyses, medical records, insurance records, can be sent via email, text message, or any other communication medium/protocol to any interested party. Likewise, an interested party (e.g. doctor, insurance company) can also send the same type of data to the personal health organizer via email, text message, or any other communication medium/protocol and the attached/transmitted data can be integrated into the records kept on the personal health organizer.

The medical data analysis module 326 can further include one or more sub-modules or programs for tracking medical data, including reading data and/or data related patient activities and correlating the medical data with patient activities. For example, the medical data analysis module 326 can track daily food intake that can be downloaded via network 124. In that embodiment, the medical data analysis module 326 is used to receive input from a user, via the input 234 and/or the display/touch panel 206, indicating food taken throughout the day. Then the medical data analysis module 326 can store the input in the storage 204, analyze the input to determine trends, and/or generate reports based on the input. This can help the physician, dietician, or patient to improve or modify dietary strategies for glucose control. In an embodiment, trending data is displayed to the user in various graphical formats on the display 206 through the medical data display module 344.

As another example, the medical data analysis module 326 can track the glycemic index (GI), which describes the effect of carbohydrates on glucose level, and is sometimes used for medical nutrition therapy. In another embodiment, the medical data analysis module 326 can maintain a log of insulin injections given and/or received to show a patient's compliance with medications. The insulin injections can be input by the user into the personal health organizer via the user interface on the display 206 or input automatically with digital syringe. The medical data analysis module 326 can also generate hypoglycemia or hyperglycemia alerts. For example, when the received reading data indicates that blood glucose is too low or too high, the medical data analysis module 326 can alert the patient and prompt the patient to log any symptoms of hypoglycemia or hyperglycemia. Moreover, the medical data analysis module 326 can have threshold reading values and/or accompanying symptom checklists configurable by a physician or a patient, so that if blood glucose values are detrimentally low or high and/or certain accompanying symptoms appear, alerts will be automatically sent to the patient's physician or emergency medical personnel. Similarly, the medical data analysis module 326 can determine if a user has missed a reading and it can send alerts (via SMS, email, automated voice call, etc.) to a friend, family member, or a caretaker to check on the user.

Moreover, the medical data analysis module 326 can calculate the amount of insulin to be given based on the user's carbohydrate intake and glucose level post-prandial. This is helpful for patients who are on an insulin sliding scale coverage. Also, the medical data analysis module 326 can perform continuous blood glucose monitoring for patients in a hospital setting or in critical care.

The medical data analysis module 326 can also be configured to manage activity flags, based on data input by a user. The data input can, by way of example, include: exercise time and severity of exercise, insulin (basal bolus) dosage, medication taken, food (GI index, carbohydrates/proteins) consumed, weight tracking, pulse rate tracking, or CO tracking for smokers. In addition, the tracking can include custom flags for other user-defined activities.

In an embodiment, the medical data analysis module 326 works with the medical data display module 344 to provide visualization of health data tracking or trending. In an embodiment, the medical data display module 344 displays trended data for a user in a variety of graphical formats, for example, when rotated in a horizontal position. The trended data can contain continuous or spot readings of measureable parameters or user input for activity flags, as discussed above.

A skilled artisan would appreciate that the medical data analysis module 326 could be associated with different types of programs or applications installed by the user that can interface with the medical data analysis module 326. The functions described herein can also be performed by the medical data analysis module 326 alone, one or more sub-modules, and/or one or more separate modules/programs on the personal health organizer.

Network Computing Support Module and Electronic Medical Data Integration Module

In addition to analyzing reading data and providing the user with reminders, alerts, and other feedback to improve the user's health, the personal health organizer in an embodiment includes the electronic medical data record integration module 322 and/or the network computing support module 302 to assist in medical data synchronization. For example, the electronic medical data record integration module 322 can provide data backup and synchronization of medical results, contacts, and other user data (music, videos, etc.). The electronic medical data record integration module 322 can also be configured to enable synchronization of emails, text messages, and voice messages. The electronic medical data record integration module 322 and/or the network computing support module 302 can also be configured to synchronize patient data to centralized medical data servers such as Google Health, Microsoft Health Vault, etc.

The electronic medical data record integration module 322 can also enable non-patients such as physicians and family members of a primary patient user to synchronize patient data with different access privileges. For instance, an alias can be created to allow non-trusted sources to review patient data without personally identifiable information. The electronic medical data record integration module 322 can further enable a user to prove good health practices and compliance to receive special discounted rates or rate cuts from health insurance providers. In an embodiment, the electronic medical data record integration module 322 and/or the network computing support module 302 include an embedded web server that allows access to locally stored history, reading/medical data, data settings, and calendar, etc.

The electronic medical data record integration module 322 and the network computing support module 302 can be associated with a calendar program. The program can allow a user to synchronize the calendar of the personal health organizer with an online synchronized calendar such as Outlook, iCalendar, Google Calendar, Yahoo Calendar, etc. The calendar can also provide an alarm function, including a smart clock that can store or access times for scheduled tests and can determine, based on reading data, if more tests are needed (invasive or non-invasive). As another example, when a prescription is entered, the personal health organizer device in an embodiment tracks medication intake and provides reminders for taking the prescribed medication.

In addition, the electronic medical data record integration module 322 can be configured such that the personal health organizer can be used by multiple users. For example, each user's data can be tracked separately on the same device. As a result, for instance, one family would only have to buy one device for spot checking, and family members can login via a password or a biometric identification system as further described below. As another example, an endocrinologist office could purchase patient licenses and store the data of patients the office spot-checks, with the patient records separated by identification tags and protected via the security features described herein. A skilled artisan would appreciate that the users' medical data (including insurance information) could be stored separately on the personal health organizer or a remote system, e.g., an Electronic Medical Record (EMR) server located on a remote computing network (e.g. cloud computing network).

In an embodiment, the medical data stored on the personal health organizer can be retrieved by an EMS or a first responder through the use of a Rad 57 or similar device. A physician can also perform data retrieval using a similar device. In another embodiment, the electronic medical data record integration module 322 can be configured to manage medical expenses and reimbursements. The electronic medical data record integration module 322 can be used to track health items purchased by the user and synchronize the items with a medical expense account. The purchased items can also be compared by a comparison shopper module/program for best prices and alternative products. The purchase history information can also be sent to insurance companies for reimbursement of co-pay overages, for example.

In another embodiment, the network computing support module 302 can be configured to provide reminders to the user if the personal health organizer is not with the user. For example, the user can call the personal health organizer via phone or send an email or text message with a particular question regarding appointment times, medication intake schedule, etc. In an embodiment, the personal health organizer or a data server with synchronized medical data records within a remote computing network (e.g. cloud computing network) provides answers to the particular questions sent.

Since diabetic patients are likely users of the personal health organizer and diabetes can sometimes lead to vision impairment, in an embodiment the electronic medical data record integration module 322 is configured to synchronize eye care prescription requirement dates and vision check-ups on a calendar. In an embodiment, the personal health organizer includes software for testing the user's vision on the device to determine if a new prescription is needed. The testing software can include Ishihara plates and distance charts displayed on the display 206, with the displayed testing materials sized according to an arm's length testing distance.

In yet another embodiment, the electronic medical data record integration module 322 is configured to coordinate prescription. For example, once a user's physician verbally mentions a prescription, the personal health organizer can acoustically identify the drug term and search for generic alternatives. Once the physician agrees to the drug (either the branded drug or the suggested generic alternative), the electronic medical data record integration module 322 is configured in an embodiment to locate a closest pharmacy (using the built-in GPS and/or triangulation software based on cell tower location) with the best price and provides contact information of the pharmacy to the user. It can also provide the pharmacy information to a remote computing network (e.g. cloud computing network) for data synchronization or send it directly to the user's physician so that he or she can submit an electronic prescription.

Various embodiments of the personal health organizer also provide for exchange of medical data and related information via email. For example, while a caregiver is taking a reading or measurement of a patient with the personal health organizer, the caregiver can ask the patient whether or how the patient would like to receive information relating to the measurement, and if the patient prefers email or text messages, the email or text message format. The caregiver can input these communication preferences and send an email or text message to the patient at the point of measurement. In one embodiment, an email of the reading or measurement is automatically sent to the patient upon the completion of measurement process. In another embodiment, the email is sent later at the direction of the caregiver user or at a time configured by the caregiver user. The email or text message could also be routed to additional supervising caregivers, medical records personnel or files, others in the health providing mechanism for a particular patient, or the like. In some embodiments, federal, state, local, caregiver facility rulemaking bodies may place requirements on the distribution and/or content of the information, including, for example, the level of permission required for certain types of data based on, for example, the content thereof. In those instances, the personal health organizer may advantageously ask the caregiver at the point of measurement to acquire the appropriate permissions, or withhold sending the email or text message until such permissions are processed, authenticated, verified, or otherwise checked and approved or the like. In other embodiments, the personal health organizer may review the available permissions and appropriate rule authorities and determine the format and content of the email or text message that is available for sending. For example, the personal health organizer may include less information, less detailed information, different groupings of medical and/or personal information based on a particular patient's permissions and/or applicable medical data disclosure rules. Other forms of electronic communications can also be used, for example, information can be posted to a website, such as a private blog. Information can also be sent through various other information posting websites such as, for example, Twitter™.

None, some, or all of the information relating to patient interactions with the personal health organizer can be sent electronically. For example, emails may be sent to those patients (e.g. an outpatient) that may take measurements on their own or have them taken by a non-professional caregiver such a family member. Emails, text messages, or other electronic communications can also include reminders, requests for data, advice based on data obtained, or any other similar personal or medical information.

Electronic Medical Data Integration Processes

Figure 6A:
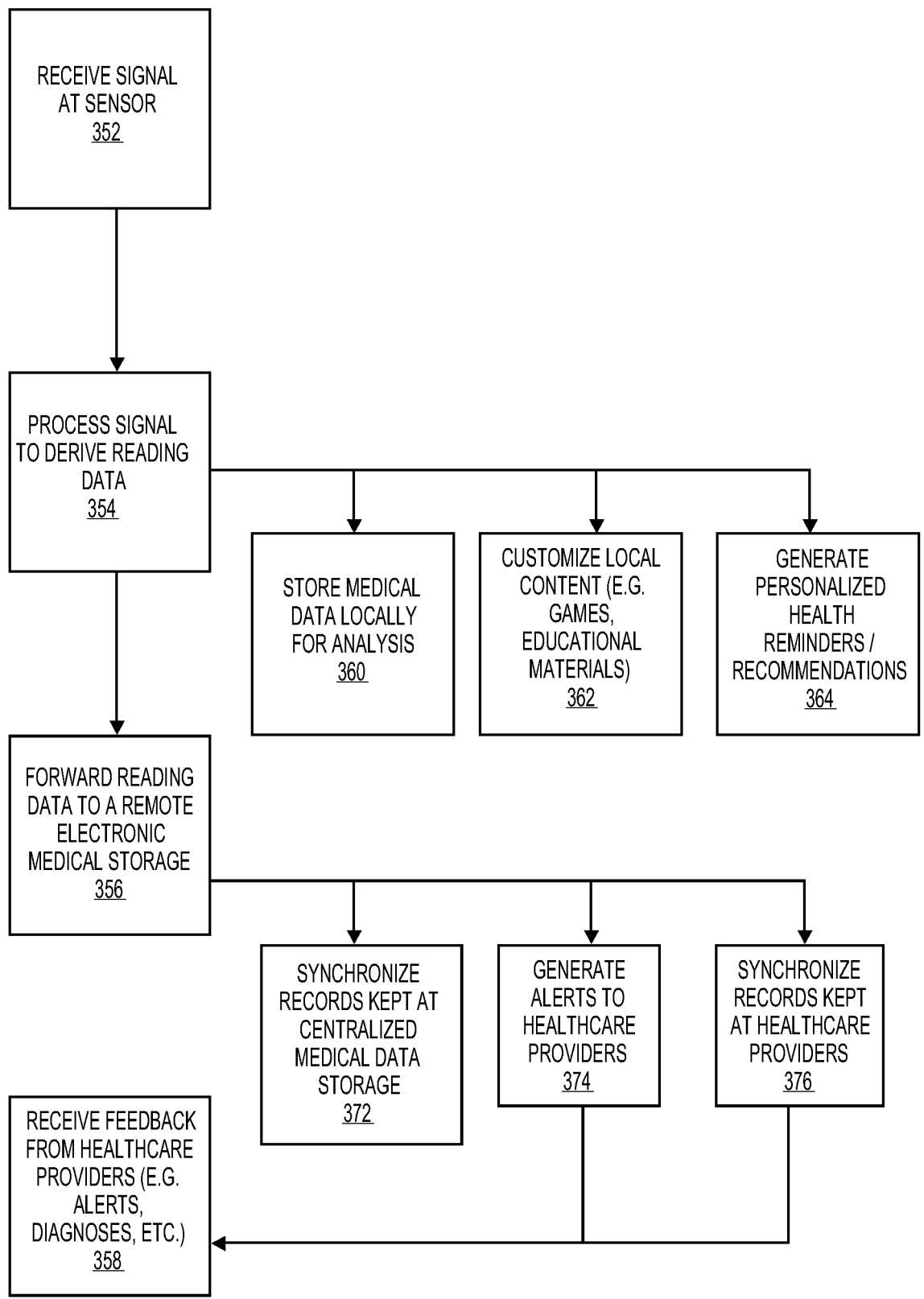
FIG. 6A is a flow diagram that illustrates various methods performed by the personal health organizer in accordance with one or more embodiments.

FIGS. 6A and 6B show methods for integrating medical data records in accordance with embodiments disclosed herein. At block 352, in an embodiment, a signal indicative of the patient physiological reading is received and/or detected at a sensor of the personal health organizer (or an associated health data collection device). At block 354, the personal health organizer (or an associated health data collection device) can process the signal to derive or calculate reading data (e.g. derive blood glucose level based on signal received). At the block 360, the reading data can be stored locally (e.g. in the storage 204) along with other medical data of the patient user. At block 362, the personal health organizer can use the reading data to customize local content at the personal health organizer, including games and educational materials. At block 364, the personal health organizer can use the reading data to generate health reminders and/or recommendations that are personalized for the patient user.

At block 356, the reading data can be forwarded to a remote electronic medical storage. In an embodiment, related medical data can be forwarded with the reading data as well. At block 372, the records kept at a centralized medical data storage can be synchronized with the forwarded reading data and/or related medical data. At block 374, the forwarded reading data and/or medical data can be used to generate alerts to healthcare providers. At block 376, the records kept at healthcare providers can be synchronized with the forwarded reading data and/or medical data. The healthcare providers can use the forwarded data to generate feedback such as alerts, data updates, and diagnoses, which are received at the personal health organizer at block 358 in accordance with an embodiment.

The synchronization of data records is further illustrated in FIG. 6B, where a patient 420 is shown to provide reading data to a personal health organizer 402, which in turns forwards the reading data and/or other related medical data of the patient 420 to a network 124. The network 124 can include a remote computing network (e.g. cloud computing network) comprising of LANs, WANs, and the Internet. The reading data can be relayed to healthcare providers 404, who can provide feedback such as alerts, reminders, and/or diagnoses to the personal health organizer 402 via the network 124. The healthcare providers 404 can also synchronize their records based on the forwarded reading data (and/or related medical data) and in turn provide synchronized and/or updated medical data back to the personal health organizer 402. Similarly, the reading data (and/or related medical data) can be forwarded to the electronic medical record storage 406 via the network, and the electronic medical record storage 406 can synchronize its records based on the forwarded reading data (and/or related medical data) and in turn provide synchronized and/or updated medical data back to the personal health organizer 402 via the network. The returned results from the healthcare providers 404 and/or the electronic medical record storage 406 can be displayed back to the patient 420 and/or used by the personal health organizer for other purposes such as completing financial costs and deductions to users' medical expense accounts.

Gaming Module

In an embodiment, the personal health organizer includes a gaming module 324 that includes and/or supports a variety of health-related games. For example, the gaming module 324 can allow the user to purchase or download games associated with health training on the disease and written to motivate the emotional state of the user. As another example, the gaming module 324 can provide a game that provides a customizable digital pet for children to disassociate from the disease but learn how to care for the digital pet and themselves. The digital pet can include interchangeable configuration data that relate to the appearance of the pet. As a further example, the gaming module 324 can display a screen saver that displays a tree either in good or failing condition depending on a user's ability to live successfully with diabetes. For example, a user with a small number of doctor visits, missed insulin injections, bad food choices, and few exercise activities can be shown a withering tree. Conversely, a user who maintains few spikes and drops can be shown a healthy, vibrant tree. In another embodiment, the gaming module 324 can provide an interactive game based on training/flash cards and tests. The cards and tests can be based on device usage, health condition/standing, disease knowledge, latest news findings on cures, etc. The testing and training can be synchronized over Internet to allow friend and group competition and participation.

The gaming module 324 can also be associated with a running companion module. The module can be used to synchronize training records for a user based on the user's shoe type or needs. The module could further be adapted to work with the accelerometer to function as a pedometer or perform some other assessment of movement. A skilled artisan would appreciate that the gaming module 324 could use measurements from the pedometer or other assessments of travel to deduce the required shoe type for a user or life span of a particular shoe. For example, the gaming module 324 can determine based on distance traveled, the best shoe type for a user or the life span of the shoe the user has been using. The gaming module 324 can utilize the accelerometer 216 in the personal health organizer to enhance the gaming experience.

External Reading from Additional Health Data Collection Devices

Embodiments of the personal health organizer include a sensor interface module 306 that is adapted to connect to sensors for measuring physiological readings of a user. In an embodiment, the personal health organizer includes the communications I/O interface module 304 that is configured to interface with various health data collection devices and to obtain reading data from those devices. For example, the personal health organizer can connect to an insulin pump to obtain performance and historical record of pump behavior and dosing. In an embodiment, the personal health organizer connects via the Bluetooth® protocol (e.g. Near Field Connect (NFC) Bluetooth 2.1 +EDR) or any other short range wireless connection protocol. In another example, the personal health organizer device can connect to a kidney urine test (sensor), which is a separate sensor adapted to scan the litmus urine test to check protein level in the blood and kidney function. This urine test reading data can be tracked along with other reading and/or patient medical data by the one or more of the modules disclosed herein, e.g., medical data analysis module 326, to detect whether changes have occurred. The detected changes can be correlated with other medical data such as medication schedules to determine whether the changes have occurred as a result of new medication or progression of disease and damage to organs.

In an embodiment, the personal health organizer is adapted to obtain reading from a weight scale (e.g. specific brands of electronics scales) to gather weight reading. In another embodiment, an optional thin pad sensor or digital scale tennis shoes can connect via a long cable or wirelessly to the personal health organizer device via, e.g., the interface component 208 shown in FIG. 4. The user stands on connected pad and the weight data is input into the medical data record of the user as kept by the personal health organizer or sent to a remote computing network (e.g. cloud computing network) for medical data synchronization.

In another embodiment, the personal health organizer is adapted to connect to a sleep sensor, which includes a finger or a toe adhesive sensor that records data to a solid state drive. The recorded data can then be downloaded to the personal health organizer device the next morning to obtain hours of reading data recorded while the user was asleep. The connection to the sleep sensor can be wireless, e.g., the personal health organizer device can near field connect (NFC) to the sensor. Optionally, the sleep sensor can include a component that sends reading data in real time to the personal health organizer device (e.g. via Bluetooth® 2.1 +EDR (300' range)), and instructs the personal health organizer to contact medical personnel or an emergency contact if the reading data indicates a urgent medical need.

In other embodiments, sensors and/or devices measuring physiological parameters such as Glucose, PR, CO, SpO2, Cholesterol, LDL, HDL, SpHb, Hemoglobin A1C, SpHet, SpMet, oxygen content, bilirubin, etc. can be connected to the personal health organizer device. In an embodiment, the interface 208 includes a universal interface that is adapted to connect to various kinds of home used medical equipment such as blood pressure measuring devices, body temperature thermometers, etc. In other embodiments, the personal health device connects these external health data collection devices through one or more wired or wireless connections as discussed above in conjunction with the interface 208 shown in FIG. 4.

Medical Information and Education—Rankings and Reviews

The personal health organizer can also include a medical information and education module 328 that provides healthcare-related information. For example, the medical information and education module 328 can download and provide endocrinologist rankings, hospital rankings, ophthalmologist rankings, podiatrist rankings, surgeon rankings, etc. Endocrinologist rankings can, for example, provide a specialist listing service for best ranked doctors in a user's area (based on GPS location or ZIP code) or elsewhere. These hospital, surgeon, and/or ophthalmologist rankings could also provide reviews based on care of diabetes. In addition or in lieu of the rankings, the medical information and education module 328 can provide diabetes product reviews. These reviews could include reviews of equipment, needles, pumps, medications, etc. These reviews and rankings can be periodically updated via the use of the network computing support module 302 and/or the communications I/O interface module 304.

Medical Information and Education—Other Information and Online Communities

In an embodiment, the medical information and education module 328 includes one or more of the following sub-modules. First, it can include a gestational diabetes sub-module that allows for the integration of information and settings specific to the term of pregnancy and the user's concerns. The gestational diabetes sub-module can show pictures of the fetus in each stage of development, and can further be synchronized with the user's calendar and week by week progression. The sub-module can also assist with monitoring timers, medication reminders, and prenatal timers etc. Second, the medical information and education module 328 can include a "Personal Nurse Educator" sub-module. The sub-module can be paid for by an insurance company to provide a 24-hour nurse on call service, with the service specifically allowed to access the user's medical information stored within a remote computing network (e.g. cloud computing network), including data stored on the personal health organizer device. The sub-module enables the user to chat with, send text messages to, email, or phone (including video conference) the on-call nurse with specific questions.

Third, the medical information and education module 328 can include an online health information and chat forum access sub-module. For example, the sub-module can provide latest information on diabetes provided by the diabetes community, including medication information, medical definitions, medical theories, leading developments in cures, and equipment available in various countries. The sub-module can also provide access to support groups. In an embodiment, the sub-module can play back recorded phonic files of correct pronunciations of medications or medical terms. Fourth, the medical information and education module 328 can include a diabetes events calendar sub-module that shows local events and/or global events about diabetes (e.g., world diabetes day, fundraisers etc.), including information on how to get involved or donate directly from the personal health organizer device.

Additional Features

In an embodiment, the personal health organizer includes the communications I/O interface module 304 for providing wireless access to the Internet. Access can be provided via any known protocols such as Wi-Fi, WiMAX, 3G, 4G, CDMA, GSM, etc. For instance, the communications module 304 can be configured to provide free Wi-Fi access at doctor's office. Similarly, communications module 304 can be associated with an IP Telephony program such as Skype. This could allow video conferencing (e.g., using built-in camera 214) between a user of the personal health organizer and his or her physician. The program can also allow Internet based calling via Vonage, Skype or other VOIP providers.

Verification/Security

In an embodiment, the device security module 342 provides a number of security features to secure data stored on the personal health organizer device or otherwise prevent unauthorized access to the device. In an embodiment, if the personal health organizer device is lost, the device security module 342 enables the device to be located with a remote computing network (e.g. cloud computing network). For example, the owner of a lost device can trace the location of the device via the GPS receiver embedded in the device, or through network address (e.g. IP address) tracing when the device is logged onto a network. Additionally, if the user misplaced the device, the device security module 342 can generate audible or visual alerts such as whistle, beep, vibrate or blink (e.g. through the audio component 244) when the user calls it or accesses it through a network.

In another embodiment, if the device is used by a new user, based on the new user's reading (e.g. blood glucose reading), the device security module 342 can recognize that the user has changed. The device can then prompt the new user to enter a password. The device security module 342 can also utilize biometric identification, for example, through the built-in camera 214. The device security module 342 can recognize the face and expressions of the user from the camera. Another embodiment includes an additional rear sub CCD or CMOS camera placed behind an LCD or OLED screen so the user could be prompted for finger print or palm identification. In addition, a CCD or CMOS camera can be embedded in the sensor to take picture of the user's finger print. In addition to or in place of external biometric identification, a special near infrared emitter detector can absorb the unique vein pattern of the finger. The device security module 342 can also utilize the CCD or CMOS camera to distinguish among patients when the device is shared among multiple patients (e.g. in a hospital setting for where a healthcare personnel is using the device for multiple patients). Once a patient's finger print is recognized, the device automatically brings up the patient's file.

Example Health Data Collection Device

Figure 7:
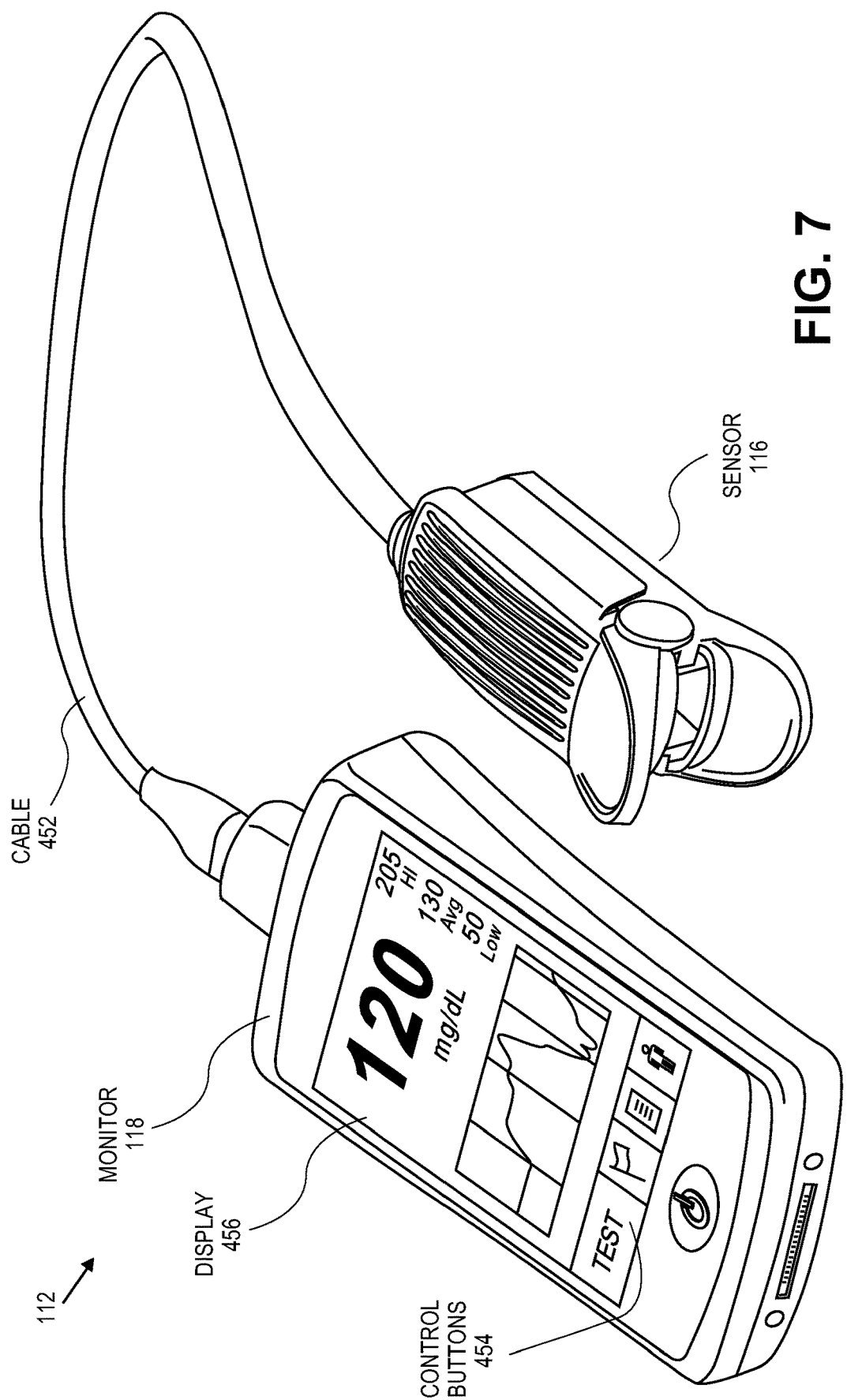
FIG. 7 illustrates a sample handheld monitor and an exemplary noninvasive optical sensor of a health data collection device in accordance with one embodiment.

FIG. 7 illustrates an example of a health data collection device 112. In the depicted embodiment, the monitoring device 118 includes a finger clip sensor 116 connected to a monitor 118 via a cable 452. In the embodiment shown, the monitor 118 includes a display 456, control buttons 454 and a power button. Moreover, the monitor 118 can advantageously include electronic processing, signal processing, and data storage devices capable of receiving signal data from said sensor 116, processing the signal data to determine one or more output measurement values indicative of one or more physiological parameters of a monitored patient, and displaying the measurement values, trends of the measurement values, combinations of measurement values, and the like.

The cable 452 connecting the sensor 116 and the monitor 118 can be implemented using one or more wires, optical fiber, flex circuits, or the like. In some embodiments, the cable 452 can employ twisted pairs of conductors in order to minimize or reduce cross-talk of data transmitted from the sensor 116 to the monitor 118. Various lengths of the cable 452 can be employed to allow for separation between the sensor 116 and the monitor 118. The cable 452 can be fitted with a connector (male or female) on either end of the cable 452 so that the sensor 116 and the monitor 118 can be connected and disconnected from each other. Alternatively, the sensor 116 and the monitor 118 can be coupled together via a wireless communication link, such as an infrared link, radio frequency channel, or any other wireless communication protocol and channel.

The monitor 118 can be attached to the patient. For example, the monitor 118 can include a belt clip or straps that facilitate attachment to a patient's belt, arm, leg, or the like. The monitor 118 can also include a fitting, slot, magnet, snap-click connector (e.g., connectors manufactured by LEMO S.A. of Switzerland), or other connecting mechanism to allow the cable 452 and sensor 116 to be attached to the monitor 118.

The monitor 118 can also include other components, such as a speaker, power button, removable storage or memory (e.g., a flash card slot), an AC or DC power port, and one or more network interfaces, such as a universal serial bus interface or an Ethernet port. For example, the monitor 118 can include a display 456 that can indicate a measurement for glucose, for example, in mg/dL. Other analytes and forms of display can also appear on the monitor 118.

In addition, although a single sensor 116 with a single monitor 118 is shown, different combinations of sensors and device pairings can be implemented. For example, multiple sensors can be provided for a plurality of differing patient types or measurement sites or even patient fingers.

Figure 8:
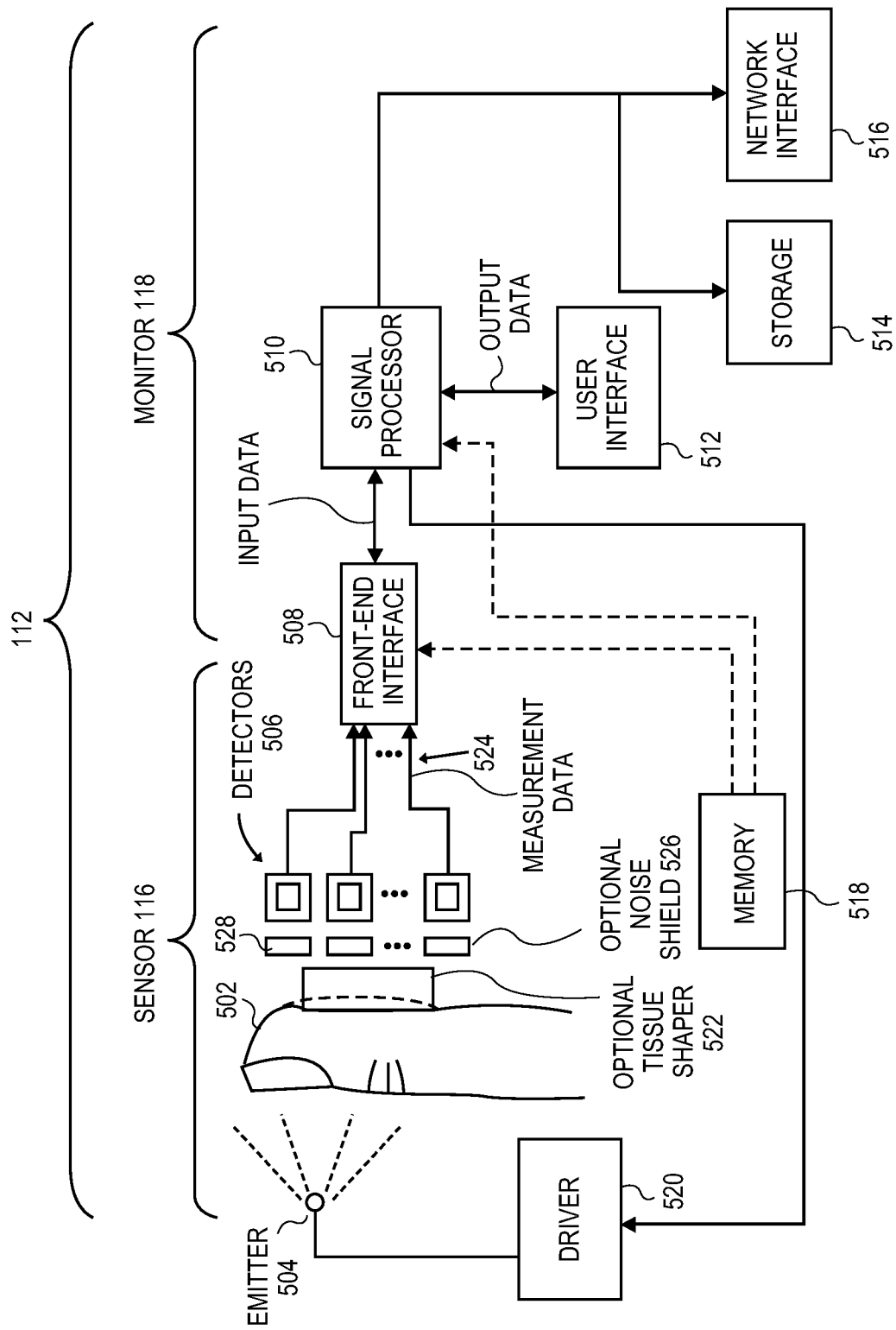
FIG. 8 is a block diagram of an example health data collection device capable of noninvasively measuring one or more blood analytes in a monitored patient, according to an embodiment of the disclosure.

FIG. 8 is a block diagram that illustrates the components of an example of a health data collection device 112. In certain embodiments, the health data collection device 112 noninvasively measures a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. The device 112 can also measure additional blood analytes and/or other physiological parameters useful in determining a state or trend of wellness of a patient.

The data collection device 112 can be capable of measuring optical radiation from the measurement site. For example, in some embodiments, the data collection device 112 can employ photodiodes defined in terms of area. In an embodiment, the area is from about 1 $mm^2$-5 $mm^2$ (or higher) that are capable of detecting about 100 nanoamps (nA) or less of current resulting from measured light at full scale. In addition to having its ordinary meaning, the phrase "at full scale" can mean light saturation of a photodiode amplifier (not shown). Of course, as would be understood by a person of skill in the art from the present disclosure, various other sizes and types of photodiodes can be used with the embodiments of the present disclosure.

The data collection device 112 can measure a range of approximately about 2 nA to about 100 nA full scale. The data collection device 112 can also include sensor front-ends that are capable of processing and amplifying current from the detector(s) at signal-to-noise ratios (SNRs) of about 100 decibels (dB) or more, such as about 120 dB in order to measure various desired analytes. The data collection device 112 can operate with a lower SNR if less accuracy is needed for an analyte like glucose.

The data collection device 112 can measure analyte concentrations, including glucose, at least in part by detecting light attenuated by a measurement site 502. The measurement site 502 can be any location on a patient's body, such as a finger, foot, ear lobe, or the like. For convenience, this disclosure is described primarily in the context of a finger measurement site 502. However, the features of the embodiments disclosed herein can be used with other measurement sites 502.

In the depicted embodiment, the device 112 includes an optional tissue thickness adjuster or tissue shaper 522, which can include one or more protrusions, bumps, lenses, or other suitable tissue-shaping mechanisms. In certain embodiments, the tissue shaper 522 is a flat or substantially flat surface that can be positioned proximate the measurement site 502 and that can apply sufficient pressure to cause the tissue of the measurement site 502 to be flat or substantially flat. In other embodiments, the tissue shaper 522 is a convex or substantially convex surface with respect to the measurement site 502. Many other configurations of the tissue shaper 522 are possible. Advantageously, in certain embodiments, the tissue shaper 522 reduces thickness of the measurement site 502 while preventing or reducing occlusion at the measurement site 502. Reducing thickness of the site can advantageously reduce the amount of attenuation of the light because there is less tissue through which the light must travel. Shaping the tissue in to a convex (or alternatively concave) surface can also provide more surface area from which light can be detected.

The embodiment of the data collection device 112 shown also includes an optional noise shield 526. In an embodiment, the noise shield 526 can be advantageously adapted to reduce electromagnetic noise while increasing the transmittance of light from the measurement site 502 to one or more detectors 506 (described below). For example, the noise shield 526 can advantageously include a conductive coated glass or metal grid electrically communicating with one or more other shields of the sensor 116 or electrically grounded. In an embodiment where the noise shield 526 includes conductive coated glass, the coating can advantageously include indium tin oxide. In an embodiment, the indium tin oxide includes a surface resistivity ranging from approximately 30 ohms per square inch to about 500 ohms per square inch. In an embodiment, the resistivity is approximately 30, 200, or 500 ohms per square inch. As would be understood by a person of skill in the art from the present disclosure, other resistivities can also be used which are less than about 30 ohms or more than about 500 ohms. Other conductive materials transparent or substantially transparent to light can be used instead.

In some embodiments, the measurement site 502 is located somewhere along a non-dominant arm or a non-dominant hand, e.g., a right-handed person's left arm or left hand. In one embodiment, the data collection device 112 can recognize a user's or patient's non-dominant arm/hand by comparing the two arms/hands according to various types of physiological data/measurements. For example, in some patients, the non-dominant arm or hand can have less musculature and higher fat content, which can result in less water content in that tissue of the patient. Tissue having less water content can provide less interference with the particular wavelengths that are absorbed in a useful manner by blood analytes like glucose. Accordingly, in some embodiments, the data collection device 112 can be used on a person's non-dominant hand or arm.

The data collection device 112 can include a sensor 116 (or multiple sensors) that is coupled to a processing device or physiological monitor 118. In an embodiment, the sensor 116 and the monitor 118 are integrated together into a single unit. In another embodiment, the sensor 116 and the monitor 118 are separate from each other and communicate one with another in any suitable manner, such as via a wired or wireless connection. The sensor 116 and monitor 118 can be attachable and detachable from each other for the convenience of the user or caregiver, for ease of storage, sterility issues, or the like. The sensor 116 and the monitor 118 will now be further described.

In the depicted embodiment shown in FIG. 8, the sensor 116 includes an emitter 504, a tissue shaper 522, a set of detectors 506, and a front-end interface 508. The emitter 504 can serve as the source of optical radiation transmitted towards measurement site 102. As will be described in further detail below, the emitter 504 can include one or more sources of optical radiation, such as LEDs, laser diodes, incandescent bulbs with appropriate frequency-selective filters, combinations of the same, or the like. In an embodiment, the emitter 504 includes sets of optical sources that are capable of emitting visible and near-infrared optical radiation.

In some embodiments, the emitter 504 is used as a point optical source, and thus, the one or more optical sources of the emitter 504 can be located within a close distance to each other, such as within about a 2 mm to about 4 mm. The emitters 504 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 504 can be arranged at least in part as described in paragraphs [0061] through [0068] of the aforementioned publication, which paragraphs are hereby incorporated specifically by reference. Other relative spatial relationships can be used to arrange the emitters 504.

For analytes like glucose, currently available non-invasive techniques often attempt to employ light near the water absorbance minima at or about 1600 nm. Typically, these devices and methods employ a single wavelength or single band of wavelengths at or about 1600 nm. However, to date, these techniques have been unable to adequately consistently measure analytes like glucose based on spectroscopy.

In contrast, the emitter 504 of the data collection device 112 can emit, in certain embodiments, combinations of optical radiation in various bands of interest. For example, in some embodiments, for analytes like glucose, the emitter 504 can emit optical radiation at three (3) or more wavelengths between about 1600 nm to about 1700 nm. In particular, the emitter 504 can emit optical radiation at or about 1610 nm, about 1640 nm, and about 1665 nm. In some circumstances, the use of three wavelengths within about 1600 nm to about 1700 nm enable sufficient SNRs of about 100 dB, which can result in a measurement accuracy of about 20 mg/dL or better for analytes like glucose.

In other embodiments, the emitter 504 can use two (2) wavelengths within about 1600 nm to about 1700 nm to advantageously enable SNRs of about 85 dB, which can result in a measurement accuracy of about 25-30 mg/dL or better for analytes like glucose. Furthermore, in some embodiments, the emitter 504 can emit light at wavelengths above about 1670 nm. Measurements at these wavelengths can be advantageously used to compensate or confirm the contribution of protein, water, and other non-hemoglobin species exhibited in measurements for analytes like glucose conducted between about 1600 nm and about 1700 nm. Of course, other wavelengths and combinations of wavelengths can be used to measure analytes and/or to distinguish other types of tissue, fluids, tissue properties, fluid properties, combinations of the same or the like.

For example, the emitter 504 can emit optical radiation across other spectra for other analytes. In particular, the emitter 504 can employ light wavelengths to measure various blood analytes or percentages (e.g., saturation) thereof. For example, in an embodiment, the emitter 504 can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitter 504 can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitter 504 can transmit any of a variety of wavelengths of visible or near-infrared optical radiation.

Due to the different responses of analytes to the different wavelengths, certain embodiments of the data collection device 112 can advantageously use the measurements at these different wavelengths to improve the accuracy of measurements. For example, the measurements of water from visible and infrared light can be used to compensate for water absorbance that is exhibited in the near-infrared wavelengths.

As briefly described above, the emitter 504 can include sets of light-emitting diodes (LEDs) as its optical source. The emitter 504 can use one or more top-emitting LEDs. In particular, in some embodiments, the emitter 504 can include top-emitting LEDs emitting light at about 850 nm to 1350 nm.

The emitter 504 can also use super luminescent LEDs (SLEDs) or side-emitting LEDs. In some embodiments, the emitter 504 can employ SLEDs or side-emitting LEDs to emit optical radiation at about 1600 nm to about 1700 nm. Emitter 504 can use SLEDs or side-emitting LEDs to transmit near infrared optical radiation because these types of sources can transmit at high power or relatively high power, e.g., about 40 mW to about 100 mW. This higher power capability can be useful to compensate or overcome the greater attenuation of these wavelengths of light in tissue and water. For example, the higher power emission can effectively compensate and/or normalize the absorption signal for light in the mentioned wavelengths to be similar in amplitude and/or effect as other wavelengths that can be detected by one or more photodetectors after absorption. However, the embodiments of the present disclosure do not necessarily require the use of high power optical sources. For example, some embodiments may be configured to measure analytes, such as total hemoglobin (tHb), oxygen saturation (SpO$_2$), carboxyhemoglobin, methemoglobin, etc., without the use of high power optical sources like side emitting LEDs. Instead, such embodiments may employ other types of optical sources, such as top emitting LEDs. Alternatively, the emitter 504 can use other types of sources of optical radiation, such as a laser diode, to emit near-infrared light into the measurement site 502.

In addition, in some embodiments, in order to assist in achieving a comparative balance of desired power output between the LEDs, some of the LEDs in the emitter 504 can have a filter or covering that reduces and/or cleans the optical radiation from particular LEDs or groups of LEDs. For example, since some wavelengths of light can penetrate through tissue relatively well, LEDs, such as some or all of the top-emitting LEDs can use a filter or covering, such as a cap or painted dye. This can be useful in allowing the emitter 504 to use LEDs with a higher output and/or to equalize intensity of LEDs.

The data collection device 112 also includes a driver 520 that drives the emitter 504. The driver 520 can be a circuit or the like that is controlled by the monitor 118. For example, the driver 520 can provide pulses of current to the emitter 504. In an embodiment, the driver 520 drives the emitter 504 in a progressive fashion, such as in an alternating manner. The driver 520 can drive the emitter 504 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 520 can be synchronized with other parts of the sensor 116 and can minimize or reduce jitter in the timing of pulses of optical radiation emitted from the emitter 504. In some embodiments, the driver 520 is capable of driving the emitter 504 to emit optical radiation in a pattern that varies by less than about 10 parts-per-million.

The detectors 506 capture and measure light from the measurement site 502. For example, the detectors 506 can capture and measure light transmitted from the emitter 504 that has been attenuated or reflected from the tissue in the measurement site 502. The detectors 506 can output a detector signal 524 responsive to the light captured or measured. The detectors 506 can be implemented using one or more photodiodes, phototransistors, or the like.

In addition, the detectors 506 can be arranged with a spatial configuration to provide a variation of path lengths among at least some of the detectors 506. That is, some of the detectors 506 can have the substantially, or from the perspective of the processing algorithm, effectively, the same path length from the emitter 504. However, according to an embodiment, at least some of the detectors 506 can have a different path length from the emitter 504 relative to other of the detectors 506. Variations in path lengths can be helpful in allowing the use of a bulk signal stream from the detectors 506. In some embodiments, the detectors 506 may employ a linear spacing, a logarithmic spacing, or a two or three dimensional matrix of spacing, or any other spacing scheme in order to provide an appropriate variation in path lengths.

The front-end interface 508 provides an interface that adapts the output of the detectors 506, which is responsive to desired physiological parameters. For example, the front-end interface 508 can adapt a signal 524 received from one or more of the detectors 506 into a form that can be processed by the monitor 118, for example, by a signal processor 510 in the monitor 118. The front-end interface 508 can have its components assembled in the sensor 116, in the monitor 118, in connecting cabling (if used), combinations of the same, or the like. The location of the front-end interface 508 can be chosen based on various factors including space desired for components, desired noise reductions or limits, desired heat reductions or limits, and the like.

The front-end interface 508 can be coupled to the detectors 506 and to the signal processor 510 using a bus, wire, electrical or optical cable, flex circuit, or some other form of signal connection. The front-end interface 508 can also be at least partially integrated with various components, such as the detectors 506. For example, the front-end interface 508 can include one or more integrated circuits that are on the same circuit board as the detectors 506. Other configurations can also be used.

The front-end interface 508 can be implemented using one or more amplifiers, such as transimpedance amplifiers, that are coupled to one or more analog to digital converters (ADCs) (which can be in the monitor 118), such as a sigma-delta ADC. A transimpedance-based front-end interface 508 can employ single-ended circuitry, differential circuitry, and/or a hybrid configuration. A transimpedance-based front-end interface 508 can be useful for its sampling rate capability and freedom in modulation/demodulation algorithms. For example, this type of front-end interface 508 can advantageously facilitate the sampling of the ADCs being synchronized with the pulses emitted from the emitter 504.

The ADC or ADCs can provide one or more outputs into multiple channels of digital information for processing by the signal processor 510 of the monitor 118. Each channel can correspond to a signal output from a detector 506.

In some embodiments, a programmable gain amplifier (PGA) can be used in combination with a transimpedance-based front-end interface 508. For example, the output of a transimpedance-based front-end interface 508 can be output to a PGA that is coupled with an ADC in the monitor 118. A PGA can be useful in order to provide another level of amplification and control of the stream of signals from the detectors 506. Alternatively, the PGA and ADC components can be integrated with the transimpedance-based front-end interface 508 in the sensor 116.

In another embodiment, the front-end interface 508 can be implemented using switched-capacitor circuits. A switched-capacitor-based front-end interface 508 can be useful for, in certain embodiments, its resistor-free design and analog averaging properties. In addition, a switched-capacitor-based front-end interface 508 can be useful because it can provide a digital signal to the signal processor 510 in the monitor 118.

As shown in FIG. 8, the monitor 118 can include the signal processor 510 and a user interface, such as a display 512. The monitor 109 can also include optional outputs alone or in combination with the display 512, such as a storage device 514 and a network interface 516. In an embodiment, the signal processor 510 includes processing logic that determines measurements for desired analytes, such as glucose, based on the signals received from the detectors 506. The signal processor 510 can be implemented using one or more microprocessors or subprocessors (e.g., cores), digital signal processors, application specific integrated circuits (ASICs), field programmable gate arrays (FPGAs), combinations of the same, and the like.

The signal processor 510 can provide various signals that control the operation of the sensor 116. For example, the signal processor 510 can provide an emitter control signal to the driver 520. This control signal can be useful in order to synchronize, minimize, or reduce jitter in the timing of pulses emitted from the emitter 504. Accordingly, this control signal can be useful in order to cause optical radiation pulses emitted from the emitter 504 to follow a precise timing and consistent pattern. For example, when a transimpedance-based front-end interface 508 is used, the control signal from the signal processor 510 can provide synchronization with the ADC in order to avoid aliasing, cross-talk, and the like. As also shown, an optional memory 518 can be included in the front-end interface 508 and/or in the signal processor 510. This memory 518 can serve as a buffer or storage location for the front-end interface 508 and/or the signal processor 510, among other uses.

The user interface 112 can provide an output, e.g., on a display, for presentation to a user of the data collection device 112. The user interface 112 can be implemented as a touch-screen display, an LCD display, an organic LED display, or the like. In addition, the user interface 112 can be manipulated to allow for measurement on the non-dominant side of patient. For example, the user interface 112 can include a flip screen, a screen that can be moved from one side to another on the monitor 118, or can include an ability to reorient its display indicia responsive to user input or device orientation. In alternative embodiments, the data collection device 112 can be provided without a user interface 112 and can simply provide an output signal to a separate display or system.

A storage device 514 and a network interface 516 represent other optional output connections that can be included in the monitor 118. The storage device 514 can include any computer-readable medium, such as a memory device, hard disk storage, EEPROM, flash drive, or the like. The various software and/or firmware applications can be stored in the storage device 514, which can be executed by the signal processor 510 or another processor of the monitor 118. The network interface 516 can be a serial bus port (RS-232/RS-485), a Universal Serial Bus (USB) port, an Ethernet port, a wireless interface (e.g., Wi-Fi such as any 802.1x interface, including an internal wireless card), or other suitable communication device(s) that allows the monitor 118 to communicate and share data with other devices. The monitor 118 can also include various other components not shown, such as a microprocessor, graphics processor, or controller to output the user interface 112, to control data communications, to compute data trending, or to perform other operations.

Although not shown in the depicted embodiment, the data collection device 112 can include various other components or can be configured in different ways. For example, the sensor 116 can have both the emitter 504 and detectors 506 on the same side of the measurement site 502 and use reflectance to measure analytes. The data collection device 112 can also include a sensor that measures the power of light emitted from the emitter 504.

Conclusion

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a shared library, or may be written in an interpreted programming language such as, for example, BASIC, Perl, Python or in a scripting language. It will be appreciated that software modules may be callable from other modules or from themselves, and/or may be invoked in response to detected events or interrupts. Software instructions may be embedded in firmware, which is stored on a memory such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While certain embodiments of the inventions disclosed herein have been described, these embodiments have been presented by way of example only, and are not intended to limit the scope of the inventions disclosed herein. Indeed, the novel methods and systems described herein can be embodied in a variety of other forms; furthermore, various omissions, substitutions and changes in the form of the methods and systems described herein can be made without departing from the spirit of the inventions disclosed herein. The claims and their equivalents are intended to cover such forms or modifications as would fall within the scope and spirit of certain of the inventions disclosed herein.

What is claimed is:

1. An electronic device for monitoring a user, comprising:
   a motion sensor configured to gather motion sensor data, of the user;
   a pulse rate sensor configured to measure pulse rate of the user;
   a location determination module configured to determine a location of the electronic device; and a processing system connected with the motion sensor,
   a location determination module, and the pulse rate sensor;
   the processing, system configured to:
     determine a location of the electronic device using the location determination module;
     monitor the pulse rate using the pulse rate sensor;
     determine a level of exercise activity based on a correlation of the motion sensor data and the monitored pulse rate;
     manage an exercise activity flag based on the determined level of exercise activity; and
     in response to determining that the pulse rate exceeds a threshold and that the user is not exercising based on the exercise activity flag:
       transmit an alert to an emergency service system;
       access one or more of a contact in an electronic address book associated with the processing system;
       determine, a proximity of the one or more of a contact relative to the determined location of the electronic device;
       contact the one or more of a contact based on the determined location of the electronic device; and
       provide the determined location of the user of the electronic device in the alert.

2. The electronic device of claim 1, wherein the emergency service system is selected based on the determined location of the electronic device.

3. The electronic device of claim 1, wherein the processing system is further configured to determine nearby medical devices or equipment and alert the user to use the nearby medical devices or equipment.

4. A method for monitoring a user of an electronic device, comprising:
   gathering, using a motion sensor, motion sensor data of the user;
   pleasuring, using a pulse rate sensor, a pulse rate of the user;
   determining a location of an electronic device, wherein the electronic device includes the motion sensor and the pulse rate sensor;
   determining a location of the electronic device using a location determination module;
   monitoring the pulse rate using the pulse rate sensor;
   determining a level of exercise activity based on a correlation of the motion sensor data and the monitored pulse rate;
   managing an exercise activity flag based on the determined level of physical activity; determining that the pulse rate exceeds a threshold and that the user is not exercising based on the exercise activity flag;
   transmitting an alert to an emergency service system based on the determination that the pulse rate exceeded the threshold and that the user is not exercising based on the exercise activity flag; accessing one or more of a contact in an electronic address book associated with a processing system;
   determining a proximity of the one or more of a contact relative to the determined location of the electronic device;
   contacting the one or more of a contact based on the determined location of the electronic device; and
   providing the determined location of the user of the electronic device in the alert.

5. The electronic method of claim 4, wherein the emergency service system is selected based on the determined location of the electronic device.

6. The electronic method of claim 4, wherein the processing system is further configured to determine nearby medical devices or equipment and alert the user to use the nearby medical devices or equipment.

* * * * *